United States Patent
Rosenkrans, Jr.

(10) Patent No.: US 8,003,328 B2
(45) Date of Patent: Aug. 23, 2011

(54) BOVINE POLYMORPHISMS AND METHODS OF PREDICTING BOVINE TRAITS

(75) Inventor: Charles F. Rosenkrans, Jr., Springdale, AR (US)

(73) Assignee: The Board of Trustees of the University of Arkansas, Little Rock, AR (US)

( * ) Notice: Subject to any disclaimer, the term of this patent is extended or adjusted under 35 U.S.C. 154(b) by 28 days.

(21) Appl. No.: 12/364,145

(22) Filed: Feb. 2, 2009

(65) Prior Publication Data
US 2009/0203020 A1 Aug. 13, 2009

Related U.S. Application Data

(60) Provisional application No. 61/025,582, filed on Feb. 1, 2008.

(51) Int. Cl.
*C12Q 1/68* (2006.01)
*C07H 21/04* (2006.01)
*C12P 19/34* (2006.01)

(52) U.S. Cl. ............................. 435/6; 536/24.3; 435/91.2

(58) Field of Classification Search ......................... None
See application file for complete search history.

(56) References Cited

OTHER PUBLICATIONS

Brym et al (Journal of Applied Genetics (2005 vol. 45, pp. 179-185).*
Websters Ninth New Collegiate Dictionary (1985) p. 1251.*
Wolf et al (Nucleic acids Research (1990) vol. 18, pp. 4905-4912).*
Brym et al (Biochem Genet (2007) vol. 45, pp. 742-754, published Oct. 11, 2007).*
Rosenkrans et al (Proceedings 61st Southern Pasture & Forage Crop Improvement Conference (2007) pp. 60-69) (May 30-Jun. 2007).*

* cited by examiner

*Primary Examiner* — Steven Pohnert
(74) *Attorney, Agent, or Firm* — Andrus, Sceales, Starke & Sawall, LLP

(57) ABSTRACT

Methods of predicting the phenotype of a trait in a bovine subject are provided. The methods include obtaining information about polynucleotide sequences specifically regarding the identity of the nucleotides present at one or more identified single nucleotide polymorphisms and using this information to make predictions regarding the trait in the subject. Also provided are kits for and methods of determining the nucleotide present in a bovine subject at a position in which a single nucleotide polymorphism is correlated with a trait.

17 Claims, 7 Drawing Sheets

SEQUENCE LISTING

<160> NUMBER OF SEQ ID NOS: 19

<210> SEQ ID NO 1
<211> LENGTH: 20
<212> TYPE: DNA
<213> ORGANISM: Artificial Sequence
<220> FEATURE:
<223> OTHER INFORMATION: Oligonucleotide

<400> SEQUENCE: 1
cgctggagtc gtacgccttc                                                    20

<210> SEQ ID NO 2
<211> LENGTH: 22
<212> TYPE: DNA
<213> ORGANISM: Artificial Sequence
<220> FEATURE:
<223> OTHER INFORMATION: Oligonucleotide

<400> SEQUENCE: 2
cttggaagta acagaaacg gg                                                  22

<210> SEQ ID NO 3
<211> LENGTH: 2369
<212> TYPE: DNA
<213> ORGANISM: Bos taurus

<400> SEQUENCE: 3
cccataaaaa cttgcggctt agtccgtgag aacagcttcc gcagacccgc tatctccaag          60
gaccgccccg agggcaccag agcttcacga tgttgatcct gtgggccgtt ttcaggtttg         120
aagcttatct cggagccgaa aaggcagggc accggcatgc cgaaaaacat ggctatcggc         180
atcgacctgg gcaccaccta ctcctgcgta ggggtgttcc agcacggcaa ggtggagatc         240
atcgccaacg accagggcaa ccgcaccacc cccagctacg tggccttcac cgataccgag         300
cggctcatcg gcgatgcggc caagaaccag gtggcgctga acccgcagaa cacggtgttc         360
gacgcgaagc ggctgatcgg ccgcaagttc ggagacccgg tggtgcagtc ggacatgaag         420
gagtggcctt ccgcgtcat caacgacgga gacaagccta aggtgcaggt gagctacaaa         480
ggggagacca aggcgttcta cccggaggag atctcgtcga tggtgctgac caagatgaag         540
gagatcgccg aggcgtacct gggccacccg gtgaccaacg cggtgatcac cgtgccggcc         600
tacttcaacg actcgcagcg gcaggccacc aaggacgcgg gggtgatcgc ggggctgaac         660
gtgctgagga tcatcaacga gcccacggcc gccgccatcg cctacggcct ggacaggacg         720 ggcaagggg agcgcaacgt gctcatctttt gatctgggag gggcacgtt cgacgtgtcc         780 atcctgacga tcgacgacgg catcttcgag gtgaaggcca cggccgggga cacgcacctg         840
ggcggggagg acttcgacaa caggctggtg aaccacttcg tggaggagtt caagaggaag         900
cacaagaagg acatcagcca gaacaagcgg ccgtgaggc ggctgcgcac cgcatgcgag         960
cgggccaaga gaaccttgtc gtccagcacc caggccagcc tggagatcga ctccctgttc        1020
gagggcatcg acttctacac gtccatcacc agggcgcggt tcgaggagct gtgctccgac        1080
ctgttccgga gcaccctaga gcccgtggag aaggcgctac gcgacgccaa gctggacaag        1140
gcgcagatcc acgacctggt cctggtgggg ggctccaccc gcatccccaa ggtgcagaag        1200
ctgctgcagg acttcttcaa cgggcgcgac ctcaacaaga gcatcaaccc cgacgaggcg        1260
gtggcgtacg gggcggcggt gcaggcggcc atcctgatgg gggacaagtc ggagaacgtg        1320

-continued

```
caggacctgc tgttgctgga cgtggctccc ctgtcgctgg gactggagac ggccggaggc    1380
gtgatgaccg ccctgatcaa gcgcaactcc accatcccca cgaagcagac gcagatcttc    1440
accacctact cggacaacca gccgggcgtg ctgatccagg tgtacgaggg cgagagggcc    1500
atgacgcggg acaacaacct gctgggcgc ttcgagctga gcggcatccc gccggccccg    1560
cgggggggtgc cccagatcga ggtgaccttc gacatcgacg ccaatggcat cctgaacgtc    1620
acggccacgg acaagagcac gggcaaggcc aacaagatca ccatcaccaa cgacaagggc    1680
cggctgagca aggaggagat cgagcgcatg gtgcaggagg cggaaaagta caaggcggag    1740
gacgaggtgc agcgcgagag ggtgtctgcc aagaacgcgc tggagtcgta cgccttcaac    1800
atgaagagcg ccgtggagga tgaggggctg aagggcaaga tcagcgaggc ggacaagaag    1860
aaggtgctgg acaagtgcca ggaggtgatt tcctggctgg acgccaacac cttggcggag    1920
aaggacgagt ttgagcacaa gaggaaggag ctggagcagg tgtgtaaccc catcatcagc    1980
agactgtacc aggggggcggg cggccccggg gctggcggct ttggggctca gggccctaaa    2040
gggggctctg ggtctggccc caccattgag gaggtggatt aggaatcctt ccctggattg    2100
ctcatgtttg ttatggagac tgttgggatc caaggctttg cattgcctta tatatctgcc    2160
tttcatcagc catcagctat gcaagctgtt tgagatgttg aactgtccct tttatgaaat    2220
taggaactct ttttttccaga gtcttaagta tagagctgaa tgtatagtgc catcttttgt    2280
cagtttcttt ttgtagtatt catgccaaac tcaagctatt tttcacccgt ttctgtttac    2340
ttccaagtaa ataaactcaa ataattcga                                     2369
```

<210> SEQ ID NO 4
<211> LENGTH: 20
<212> TYPE: DNA
<213> ORGANISM: Artificial Sequence
<220> FEATURE:
<223> OTHER INFORMATION: Oligonucleotide

<400> SEQUENCE: 4
gaagagcgcc gtggaggatg    20

<210> SEQ ID NO 5
<211> LENGTH: 20
<212> TYPE: DNA
<213> ORGANISM: Artificial Sequence
<220> FEATURE:
<223> OTHER INFORMATION: Oligonucleotide

<400> SEQUENCE: 5
gccaggaaac cagagacaga    20

<210> SEQ ID NO 6
<211> LENGTH: 20
<212> TYPE: DNA
<213> ORGANISM: Artificial Sequence
<220> FEATURE:
<223> OTHER INFORMATION: Oligonucleotide

<400> SEQUENCE: 6
cctacgcagg agtaggtggt    20

<210> SEQ ID NO 7
<211> LENGTH: 1315
<212> TYPE: DNA
<213> ORGANISM: Bos taurus

<400> SEQUENCE: 7

```
gaattcggga ctcaggttaa tccaggcacc actgatcatc cgaggctgaa ccaggaattt     60
aaaaggcaca gaggagggga ggggtgcgtc cgcacctggg gctgggaaag atgaggaatc    120
cggagaagcg caaaggacag ctaaatatcc tatggaaaat attttctttc tcaagcccag    180
tccagcccga ggagaaaggg agcagctctg ggcggggaca ggggcgctgt ggctccagcc    240
ctgcccttcc acgctccccc gaccgagcag gtcccttcta aggcgttggg aaccttctac    300
aatctaaaaa ccatatacct aattgatttt cttctgaaaa ttaaaatttc cctcccatc     360 tgaatagggc taagaggag ccaaaactta aatagcttca actctctcct tttccttccc     420
attttaaaaa taagatggga aaagcgccgc ggatgaccaa ggcatttctc ggacagcccg    480
gccgctcggc gagccagccc aaacgtggct gcttccatca gcgttagcct ccgatcactc    540
tccttggccc acagatagcc aaccctcttc gagaaactcg ggaactttct gtattttggc    600
tgtcccggca gtcgtgtagc ccttaattct actttaaacc accaaactaa tttgagcccc    660
gagatcctct caccgcccta caattaatta caagcccagg gctgatcctt ccagtcgact    720
cgactccaaa ctacttggct ggctggtcgc caggaaacca gagacagagt gggtggacct    780
tcccagcccc tctcccccctc tccttaggac tcctgtttcc tccagcgaat cctagaagag    840
tctggagagt tctgggagga gaggcatcca gggcgctgat tggttccaga aagccagggg    900
gcaggacttg aggcgaaacc cctggaatat tcccgacctg gcagcccac tgagctcggt     960 cattggctga cgagggaaaa ggcggggctt gatgaagaat tataaacaca gagccgcctg   1020
aggagaaaca gcagcctgga gagagctgat aaaacttacg gcttagtccg tgagagcagc   1080
ttccgcagac ccgctatctc caaggaccgc ccgaggggca ccagagcgtt cagttttcgg   1140
gttccgaaaa gcccgagctt ctcgtcgcag atcctcttca ccgatttcag gtttgaagct   1200
tatttcggag ccggaaaagc agggcaccgg catggcgaaa aacacagcta tcggcatcga   1260
cctgggcacc acctactcct gcgtaggggt gttccagcac ggcaaggtgg agatc        1315
```

<210> SEQ ID NO 8
<211> LENGTH: 1786
<212> TYPE: DNA
<213> ORGANISM: Bos taurus

<400> SEQUENCE: 8

```
gtgcatccca gtcccagcca aaggcctgag aagtcggagt gtcagcagtc tggcagctat     60
taatcggtgc cccaggtgca tggaggaagt ggattcacct ataccttaa aacattcatg    120 ggcaggtagg acaggttcct ttagggtcta agtccaagat ggcaactctc aaggatcagc    180
tgattcagaa tcttcttaag gaagaacatg tcccccagaa taagattaca attgttgggg    240
ttggtgctgt tggcatggcc tgtgccatca gtatcttaat gaaggacttg gcagatgaag    300
ttgctcttgt tgatgtcatg gaagataaac tgaagggaga gatgatggat ctccaacatg    360
gcagcctttt ccttagaaca ccaaaaattg tctctggcaa agactataat gtgacagcaa    420
actccaggct ggttattatc acagctgggg cacgtcagca gagggagag agccgtctga    480 atttggtcca gcgtaacgtg aacatcttta aattcatcat tcctaatatt gtaaaataca    540
gcccaaattg caagttgctt gttgtttcca atccagtcga tattttgacc tatgtggctt    600
ggaagataag tggctttccc aaaaaccgtg ttattggaag tggttgcaat ctggattcag    660
ctcgcttccg ttatctcatg ggggagaggc tgggagttca cccattaagc tgccatgggt    720
ggatccttgg ggagcatggt gactctagtg tgcctgtatg gagtgagtg aatgttgctg    780 gtgtctccct gaagaattta caccctgaat taggcactga tgcagataag gaacagtgga    840
```

```
aagcggttca caaacaagtg gttgacagtg cttatgaggt gatcaaactg aaaggctaca      900
catcctgggc cattggactg tcagtggccg atttggcaga aagtataatg aagaatctta      960
ggcgggtgca tccgatttcc accatgatta agggtctcta tggaataaaa gaggatgtct     1020
tccttagtgt tccttgcatc ttgggacaga atggaatctc agacgttgtg aaagtgactc     1080
tgactcatga agaagaggcc tgtttgaaga agagtgcaga tacactttgg gggatccaga     1140
aagaactgca gttttaaagt cttctaatgt tgtatcattt cactgtctag ctacacagg      1200 attttagttg gaggttgtaa ttcatattgt cctttatatc tgatctgtga ttaaaacagt     1260
aatgttaaga cagcctagga aaaatcaat  ttcctaatgt tagaaatagg aatggttcat     1320
aaaaccctgc tggatggcaa ggaatggttc atgaaacctt gcagctgtac cctgatgctg     1380
gatggcactt accttgtgtg gtcctaaatt ggtttgtcaa ataattcaac ttcctcaaga     1440
ggtaccactg cccatgttgc agatgctaca gttgcccttc aaaccagatg tgtatttact     1500
gtgtaatata acctctggtt cctttagcca aggtgcctag tccaactttt ttccctccag     1560
ttgatcactt cctgggatcc aatgtacaaa tccagtattg catgccatgt gctaaactgt     1620
tctaaagaat cttatgtact gtatgtatca gaatagtgta cattgccttg taatgtaaaa     1680
agggaaaatt acataaataa tgcaaccaac taagttatac caactaaaac aataaataaa     1740
gcttgaacag tgactactct gttaattaag aaaaaaaaaa aaaaaa                    1786

<210> SEQ ID NO 9
<211> LENGTH: 20
<212> TYPE: DNA
<213> ORGANISM: Artificial Sequence
<220> FEATURE:
<223> OTHER INFORMATION: Oligonucleotide

<400> SEQUENCE: 9
tccaagatgg caactctcaa                                                   20

<210> SEQ ID NO 10
<211> LENGTH: 20
<212> TYPE: DNA
<213> ORGANISM: Artificial Sequence
<220> FEATURE:
<223> OTHER INFORMATION: Oligonucleotide

<400> SEQUENCE: 10
tgaatccaga ttgcaaccac                                                   20

<210> SEQ ID NO 11
<211> LENGTH: 1319
<212> TYPE: DNA
<213> ORGANISM: Bos taurus

<400> SEQUENCE: 11
gcgcgcctgc aggtcgacac tagtggatcc aaagaattcg gcacgagctg actttgtctt       60
cgtgcagccc ttatcactct ctggagaact ttctctcccc tgggcacaat ggcaactctt      120
aaggaaaaat tgattgcacc agttgcagaa gaagagacaa cgatcccaaa caataagatc      180
actgtagtgg gtgttggaca agttggtatg gcatgtgcca tcagcattct gggaaagtct      240
ctgactgacg agcttgctct tgtggatgtt ttggaagata aactcaaagg agaaatgatg      300
gacctgcagc acgggagctt attccttcag acaccaaaaa ttgtggcaga caaagattac      360
tctgtcactg ccaattccaa gatcgtggtg gtaactgcag gagttcgcca gcaagaaggg      420
gagagtcgcc tgaatttggt gcaaaggaac gttaacgtct tcaagttcat cattcctcag      480
```

```
atcgtcaagt acagtcctgc ctgcatcatc attgtggttt ccaacccagt ggatattctc      540
acatatgtta cctggaaact aagtggatta cccaagcacc gtgtgattgg gagtggatgt      600
aacctggatt ctgctagatt tcgctacctt atggctgaaa acttggcat tcatcccagc      660 agctgccacg gatggatttt ggggggaacat ggcgactcaa gcgtggctgt gtggagtgga     720
gtgaatgtgg caggcgtttc tctccaggaa ctgaatccag aaatgggaac agacaatgat     780
agtgaaaatt ggaaggaagt gcataagatg gtggttgaga gtgcctatga agtcatcaag     840
ctaaaaggat ataccaactg ggctattgga ttaagtgtgg ctgatcttat tgaatccatg     900
ttgaaaaatc tatcgaggat tcacccagtg tcaacaatgg tgaagggcat gtatggcatt     960
gagaatgaag tcttcctgag ccttccgtgt atcctgaatg ctcgagggtt aaccagtgtt    1020
atcaaccaga agctgaagga tgaagaggtt gctcaactca agaaaagtgc agacaccctc    1080
tggggcatcc aaaaggacct gaaggacctg tgacttccgg ctgcaaggct gtagacactt    1140
agcaactaca gtgtgattaa ccacaagcct ttagtttgca tccatgtaca tggagcacag    1200
ttcgcttttg tcttccttaa gtctgtgaat ctgggctccc agaatcaaag cccatgcttg    1260
ctttaatgct gcaagatga gtccttgaac aaatcaaata aaccacctag tgtagtgtg     1319

<210> SEQ ID NO 12
<211> LENGTH: 20
<212> TYPE: DNA
<213> ORGANISM: Artificial Sequence
<220> FEATURE:
<223> OTHER INFORMATION: Oligonucleotide

<400> SEQUENCE: 12
gtacagtcct gcctgcatca                                                   20

<210> SEQ ID NO 13
<211> LENGTH: 20
<212> TYPE: DNA
<213> ORGANISM: Artificial Sequence
<220> FEATURE:
<223> OTHER INFORMATION: Oligonucleotide

<400> SEQUENCE: 13
ccattgttga cactgggtga                                                   20

<210> SEQ ID NO 14
<211> LENGTH: 2209
<212> TYPE: DNA
<213> ORGANISM: Bos taurus

<400> SEQUENCE: 14
gatctgggtc gacctgcagg tcaacggatc tgcaaaagag cacatacaaa aattaaggta      60
gataggcagt gacatatgag aaagacagat aagacagtta tgacatttta tataaaataa     120
gccttttaca ttatttcaac ccactccagg tctcttgcct ggaaaatccc atggatggag     180
gagactggta ggctgcagtc catggggtca ctaggagtca gacgtgactg agcgacttca     240
ctttcccttt tcagtttcat gcattggaga aggaaatggc aacccactcc agtattcttg     300
cctggagaaa cccagggatg ggagagcctg gagggctgcc gtctatgggg tcgcccagag     360
tcagatacga ctgaagcgac ttagcagcag cagcagtttg cattatttag ctatggcagt     420 atcctttta caggaaatat agggctgtga atcagcaaga aagcacacaa gaaatttac      480 agagaaacat ggacctcttc ggaatcaaat agatcagttg gcctccattg aataaacaac     540
ttaggctttt taaattactt ttttcctcgc tatctacaaa aggtaaagca cctttaaatt     600
```

-continued

```
ttaagattaa gttgtcaatt cttagggcag attttcctat tattaagttt caggaaagga    660
ggggaaattg gggcagcatt aatttcttta caaatggcac tgttctcaac aactcagact    720
ttcactgtcc agggaaaaac agataccaag catggcattt tgacccagct ttaagttgac    780
ggagtctatg tagcatcata cttgattcat ttgatgcaaa atcagtattg attaagctaa    840
ggcagttagg aggatagttt ttaagtggcg ttagtctttg ttatgatttc taagtcccca    900
taagcacact tggataattg ctaaagcaaa atacagcagg agaaactata gaaaatatga    960
atgcaataaa aagagattat tttcttaatg cagctcactt gtcaatttac tctgagagac   1020
atatggtaaa attgaaacta aaggtcacag gctgcttgag atgcatgaac ttaaaaatta   1080
aagaaagtca tcagcaactt ggtctatatt cattaccatc atctcattca ggaaatctct   1140
aaaaggcaag tggaaccttta gagcccatga aagatgaatt tttgtcacct tggccctaga   1200
gtggcttgag gtcagagaat taaagctatc ataagttaat aacagtttgt gtaaccttac   1260
ccttaaggaa agtgaacatg actgtctaga attttgtttt actgcattta ccagagtttg   1320
tgtgtgtgtg tatgtgtgtg tgtgcccttg aaaaccactg tcacttcccc agtatgaact   1380
ccctaaagtt aggggtgagt tttgtgttca ttgtagaaga gagggcaacg tatgttggag   1440
gattcatttt ccagccctct tcacatccct cctgatttct cttgaagtga taaacatttc   1500
ggtatctaac ttgactaatt ctatatcctt gacatttaaa ctccccatcc cactgtttct   1560
caatctgggg acgaaagata taactttaca tacatgttaa aatcaaaaga cttatgtgaa   1620
aatgcacatt ttaccacaga gatatatcct tttagaaagg acaaaacaga atgtgtaaaa   1680
atcaagaaaa aaaaaatgag gaaaatgtat tgagagtata acaggaactg aaaatcttac   1740
ttactcatcc ttattctata tttcttagta tttagtgtgt aaattttgaa atcttgactt   1800
cagccagcaa ttttgaatga gaataaaata ctctttgata atacatgaga cacctaagtg   1860
aaagataatg ctatattcaa gaaactgcag agaaataaag gcaatgttca caagaaatga   1920
ctgctataat tttatagttc ctctaactca aactagtctc cagatctcac catcattatc   1980
tctctcattt cctttcagtc taattaatca aaatccttcc tagatgttca tttctggtca   2040
gtatgtcttc ctgaatatga ataagaaata gaataccatt caatgtttga aatttatggg   2100
gtaatctcaa tgacggaaat agatgactgg caaaagggaa gggaatgcct gattaaatat   2160
attcatgaag atgtcaaagc cttataaagc caacatctgg ggaagagaa              2209
```

<210> SEQ ID NO 15
<211> LENGTH: 22
<212> TYPE: DNA
<213> ORGANISM: Artificial Sequence
<220> FEATURE:
<223> OTHER INFORMATION: Oligonucleotide

<400> SEQUENCE: 15
aagtccccat aagcacactt gg                                              22

<210> SEQ ID NO 16
<211> LENGTH: 23
<212> TYPE: DNA
<213> ORGANISM: Artificial Sequence
<220> FEATURE:
<223> OTHER INFORMATION: Oligonucleotide

<400> SEQUENCE: 16
ctaactttag ggagttcata ctg                                             23

<210> SEQ ID NO 17

<211> LENGTH: 1870
<212> TYPE: DNA
<213> ORGANISM: Bos taurus

<400> SEQUENCE: 17

| | | | | | |
|---|---|---|---|---|---|
| cggatggaac | tgatcccaag | cttttccatg | gaaacctggg | ttctcctagc | taccagcctg | 60 |
| gtgctcctct | atatatatgg | gacttattca | tatggacttt | ttaagaagct | ggggattcct | 120 |
| gggccaagac | ctgtgcccta | ttttggaagt | actatggctt | accacaaggg | tattccagag | 180 |
| tttgacaatc | agtgttttaa | aaagtatggg | aaaatgtggg | ggttttatga | aggtcgacaa | 240 |
| cctatgttgg | ctatcacaga | tcctgatata | atcaaaacag | tactagtgaa | agaatgttat | 300 |
| tctgtcttca | caaaccggag | gattttggt | ccaatgggaa | ttatgaaata | tgccatctct | 360 |
| ctggcttggg | atgaacaatg | gaagagaata | cggacattgc | tgtctccagc | cttcaccagc | 420 |
| ggaaagctca | aggagatgtt | ccccatcatt | ggccagtatg | agatatgtt | ggtgaggaac | 480 |
| ctgaggaagg | aagcagagaa | aggcaatccc | gtcaacatga | agacatgtt | tggagcctac | 540 |
| agcatggatg | tgattactgg | cacagcattt | ggagtgaata | ttgattccct | caacaaccca | 600 |
| cacgatccct | tgtggaaca | tagcaagaac | ctcttaagat | ttagacccct | cgatccattc | 660 |
| attctttcaa | taatattatt | tccatttctc | aacccagttt | ttgaaatatt | aaacattact | 720 |
| ctgtttccaa | aaagtactgt | ggactttttc | acaaaatctg | taagaagat | taagaaagt | 780 |
| cgcctcacag | ataaacaaat | gaatcgagtg | gatttacttc | agctaatgat | taattctcag | 840 |
| aattccaaag | aaattgacaa | ccataaagct | ctgtctgaca | tagaactcgt | ggcccaaagt | 900 |
| actatcttta | ttttggtgg | ctatgagacc | actagcagta | ctctttcctt | cattatatat | 960 |
| gaattgacca | ctcaccctca | tgtccagcag | aagctgcagg | aggaaattga | tgcaactttc | 1020 |
| cctaataagg | cccctcccac | ctacgatgcc | ctggtgcaga | tggagtatct | tgacatggtg | 1080 |
| gtgaatgaga | ctctgagaat | gttttccaatt | gctgggagac | ttgagagggg | ctgtaagaag | 1140 |
| gatgtggaaa | tccacggggt | gaccattccc | aaagggacaa | ccgtgctggt | gccactcttc | 1200 |
| gttcttcaca | caaacccaga | gctctggcca | gagcccgagg | agttccgtcc | cgaaaggttc | 1260 |
| agtaagaata | caaggacag | cataaatcct | tacgtctacc | tgccttttgg | aactggaccc | 1320 |
| cgaaactgcc | ttggcatgag | gtttgccatc | atgaacataa | aacttgctct | tgtcagaatc | 1380 |
| ctgcagaact | tctccttcaa | accttgtaaa | gaaacacaga | tcccccctgaa | attatacact | 1440 |
| caaggactca | cgcagccaga | acaacctgtt | attctgaagg | ttgtgcccag | aggcctggga | 1500 |
| ccacaggtgg | agcctgactt | tctctaagga | tttgcacttc | ggttttgaag | gaagctgcat | 1560 |
| ctcagaacac | cagagacgtg | gtctactttg | ataaagccaa | taataaaga | tgggcttcac | 1620 |
| ctactgtact | tgctggtgag | tagggttctg | cataatcatt | tagctttctc | gctgcctacc | 1680 |
| tggattatta | gatactacgt | accatacaaa | ggaggtgatt | agcaagtgcc | agatactcaa | 1740 |
| cttcacaggt | tctcatagga | cactctccat | ccaccccagt | tagtactatc | tactcctcct | 1800 |
| gagcactgat | cagaatgaag | atctctcaac | aatcttatcg | acagacttta | atgaaaataa | 1860 |
| gaattaaaat | | | | | | 1870 |

<210> SEQ ID NO 18
<211> LENGTH: 21
<212> TYPE: DNA
<213> ORGANISM: Artificial Sequence
<220> FEATURE:
<223> OTHER INFORMATION: Oligonucleotide

<400> SEQUENCE: 18

```
caacaacatg aatcagccag a                                              21
```

<210> SEQ ID NO 19
<211> LENGTH: 21
<212> TYPE: DNA
<213> ORGANISM: Artificial Sequence
<220> FEATURE:
<223> OTHER INFORMATION: Oligonucleotide

<400> SEQUENCE: 19

```
cctacattcc tgtgtgtgca a                                              21
```

BOVINE POLYMORPHISMS AND METHODS OF PREDICTING BOVINE TRAITS

CROSS-REFERENCE TO RELATED APPLICATIONS

This application claims priority to U.S. Provisional Patent Application No. 61/025,582, filed Feb. 1, 2008, which is incorporated herein by reference in its entirety.

STATEMENT REGARDING FEDERALLY SPONSORED RESEARCH

This invention was made with government support under Grant No. ARS Cooperative Agreement #58-6227-8-040, awarded by the United States Department of Agriculture. The government has certain rights in the invention.

SEQUENCE LISTING

A sequence listing accompanies this application and is incorporated herein by reference in its entirety. The sequence listing was filed with the application on Feb. 2, 2009 as a text file.

BACKGROUND

Traditionally, selective breeding has been used to produce livestock, such as cattle, with desirable characteristics or traits. The selected traits may relate to the reproductive capability, the strength and growth potential of the offspring, the ability to tolerate temperature extremes, milk or meat quality, and resistance to disease. Selective breeding is imprecise and often offspring do not possess the traits or characteristics of the parents. Additionally, it is often difficult to predict which offspring would be best suited for various applications.

SUMMARY

Methods of predicting a trait in a bovine subject are provided. The methods include obtaining information about a polynucleotide sequence selected from LDH-B, LDH-A, P450, HSP70, the HSP70 promoter, and the prolactin promoter of the bovine subject. The information is then used to predict the trait in the bovine subject.

In another aspect, polynucleotides encoding at least a portion of bovine LDH-B, LDH-A, cytochrome P450, HSP70, the HSP70 promoter, or the prolactin promoter comprising a disclosed set of polymorphisms are provided.

In yet another aspect, methods of determining a nucleotide in a bovine subject at a position in which a single nucleotide polymorphism is correlated with a trait are provided. The methods include detecting a target polynucleotide in a bovine sample with at least one oligonucleotide capable of binding the target polynucleotide. The target polynucleotide comprises a single nucleotide polymorphism (SNP) disclosed herein. The nucleotide at the SNP in the bovine subject is then identified.

In still another aspect, kits including a first oligonucleotide capable of binding to a target polynucleotide are provided. The target polynucleotides comprise the SNPs described herein. The kits also include instructions for determining the nucleotide at the SNP position.

In yet another aspect, methods of predicting the occurrence of a trait in a bovine subject are provided. The methods include identifying a nucleotide of the bovine subject. The nucleotide is selected from an adenine at position 541 of LDHB, an adenine at position 606 of LDHB, a thymine at position 652 of LDHB, a thymine at position 669 of LDHB, a guanine at position 618 of LDHB, an adenine at position 390 of LDHA, a cytosine at position 530 of LDHA, a guanine at position 994 of cytochrome P450, a guanine at position −1161 of the prolactin promoter, a thymine at position −1286 of the prolactin promoter, a cytosine at position −895 of the HSP70 promoter, an adenine at position −1045 of the HSP70 promoter, a thymine at position −1069 of the HSP70 promoter, a guanine at position −1096 of the HSP70 promoter, an adenine at position −1117 of the HSP70 promoter, a cytosine at position −1125 of the HSP70 promoter, a thymine at position −1128 of the HSP70 promoter, a cytosine at position −1134 of the HSP70 promoter, a guanine at position −1154 of the HSP70 promoter, a cytosine at position −1204 of the HSP70 promoter, an adenine at position 1851 of HSP70, an adenine at position 1899 of HSP70, a thymine at position 1902 of HSP70, a thymine at position 1917 of HSP70, a guanine at position 1926 of HSP70, a cytosine at position 2033 of HSP70, a guanine at position 2087 of HSP70 and an adenine at position 2098 of HSP70. The identity of the nucleotide at the indicated position is correlated to the occurrence of the trait in the bovine subject. Thus, the identity of the nucleotide is predictive of the occurrence of the trait.

DETAILED DESCRIPTION

Figure 1:
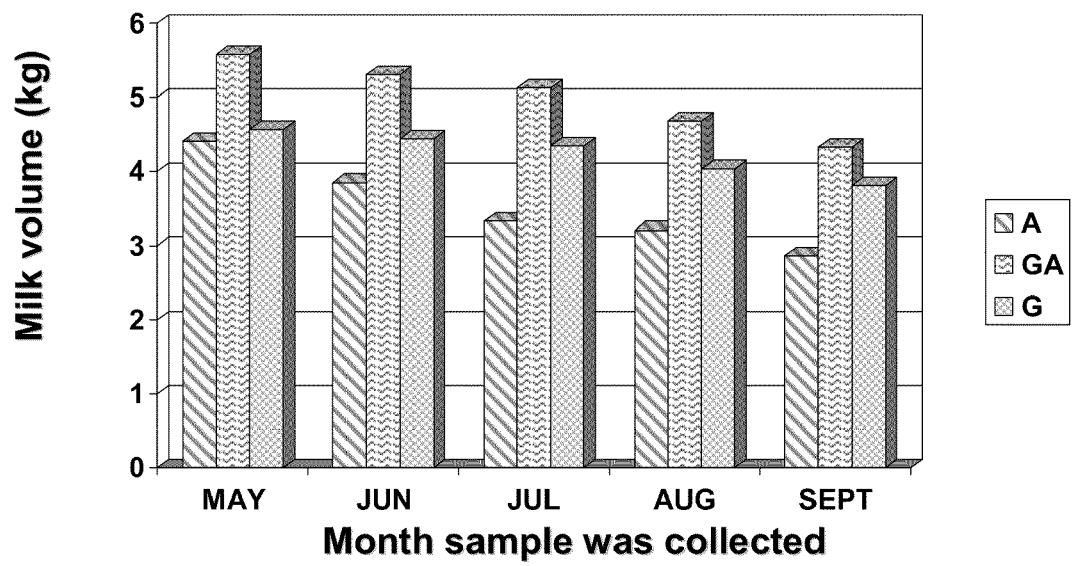
FIG. 1 is a graph showing the effect of different genotypes at position 606 of the polynucleotide encoding bovine LDH-B on the volume of milk produced by bovine subjects.

A method of predicting a trait in a bovine subject is provided. The method includes obtaining information about a polynucleotide sequence of the bovine subject. The information is predictive of the trait. As described in the Examples, single nucleotide polymorphisms may be detected within polynucleotide sequences of bovine subjects. It was discovered that some of these polymorphisms are predictive of the breed lineage or parentage of the bovine subject and others predictive of other traits of the bovine subject or of offspring produced by the bovine subject, such as fertility, milk production, and susceptibility to fescue toxicosis. These methods allow the identification and selection of cattle with superior potential for desirable characteristics or traits.

The methods, compositions and kits provided herein may be used to manage a cattle herd. For example, animals may be selected for mating, breeding, or cloning of cattle or for milk or meat production qualities. The methods allow cattle to be identified and monitored for key traits or characteristics in individual animals or within a herd. Such identification and monitoring of animals allows animals to be used for their highest end use and best potential for performance. Animals may be identified for breeding, milk production, or meat production or may be selected to mate because of the potential to produce offspring with increased potential for such characteristics and improved animal health and well-being. The methods, kits and compositions provided herein allow for the identification and selection of cattle with genetic potential for particular traits.

The information obtained about the polynucleotide sequence generally includes the identity of at least one nucleotide present at a particular position within the genome of the individual animal where a single nucleotide polymorphism (SNP) is identified. Polymorphisms are allelic variants that occur in a population that can be a single nucleotide difference present at a locus, or can be an insertion or deletion of one, a few or many consecutive nucleotides. A SNP is characterized by the presence in a population of two, three or four nucleotides (i.e., adenosine, cytosine, guanosine or thymidine) or an insertion or deletion of at least one nucleotide at a particular locus in genomes from different animals. Typically less than all four nucleotides will occur at a single SNP site.

Several SNPs are described below and in the Examples. The Examples below demonstrate that the presence of a particular nucleotide in a specific identified SNP position is linked to the expression of a trait in the individual. Thus the identity of the nucleotide(s) present in the animal at the SNP site may be indicative of animals with a particular phenotype related to a trait. The identity of the nucleotide(s) present at the SNP in an individual may be used to predict whether the individual is likely to have a trait or express a particular phenotype related to the trait as compared to other animals. Predicting and prediction as used herein includes, but is not limited to, generating a statistically based indication of whether a particular subject will have a particular trait or express a particular phenotype. Predicting may also include using the statistical information found in the Examples or generated by another entity to generate predictions about a bovine subject. This does not mean that the trait or phenotype will occur with 100% certainty.

The polynucleotide sequence may be selected from the polynucleotide sequences of LDH-B, LDH-A, cytochrome P450, HSP70, the HSP70 promoter and the prolactin promoter or a combination thereof. The Examples identify several single nucleotide polymorphisms relative to the published sequence of these polynucleotides on GenBank. Single nucleotide polymorphisms linked to particular traits were identified at positions 541, 606, 618, 652 and 669 of the LDH-B polynucleotide sequence (SEQ ID NO: 11); at positions 390 or 530 of the LDH-A polynucleotide sequence (SEQ ID NO: 8); at position 994 of the prolactin sequence (SEQ ID NO: 17); at positions −1286, −1161, or −1134 relative to the prolactin start site (prolactin promoter sequence SEQ ID NO: 14); at positions −895, −1045, −1069, −1096, −1117, −1125, 1128, −1134, 1154 or −1204 relative to the start site of the HSP70 polynucleotide sequence (HSP70 promoter sequence SEQ ID NO: 7); and at positions 1851, 1899, 1902, 1917, 1926, 2033, 2087 or 2098 of the HSP70 polynucleotide sequence (SEQ ID NO: 3). These SNP sites linked to specific traits are also referred to as the "associated SNPs".

The information about the polynucleotide sequence may be obtained by any method, including those known to those of skill in the art. For example, the information may be obtained by sequencing, restriction fragment length polymorphism (RFLP) analysis, differential amplification, primer extension or microarray analysis. Alternatively, the information can be obtained from a separate entity, such as an independent testing laboratory.

Some of the polymorphisms result in an amino acid change in the polypeptide encoded by the polynucleotide. These single nucleotide polymorphisms can be detected and information about the polynucleotide obtained by any method capable of detecting amino acid changes in a polypeptide, e.g., using protease digestion or Western blot analysis. In the Examples, the polynucleotides from individual bovine subjects were amplified using polymerase chain reaction and information was obtained with RFLP analysis or nucleotide sequencing.

The methods may be used to predict a wide variety of traits of the animals tested, including but not limited to, breed lineage, parentage, calving rate, calf weight at birth, calf weight at weaning, calf height at weaning, body condition (a visual appraisal of body fat), susceptibility to fescue toxicosis, prolactin concentrations, milk production, milk quality (including milk butterfat concentrations, milk protein concentrations, and milk somatic cell count), hormone concentrations, LDH concentration, fertility, disease resistance (including parasite load), feed lot gain, meat quality, and carcass composition. For example, milk quality and production may be assessed by the volume of milk production, the percent of butterfat and protein in the milk, the ability to produce milk over time, the somatic cell count of the milk and the effect of different food sources on the milk. Meat quality may be assessed by the extent of marbling in the meat, the United States Department of Agriculture (USDA) grade of the meat, the quantity of meat (USDA yield grade), carcass fat quantity, muscle content, and taste panel perception of beef or a variety of other factors available to those skilled in the art. Those of skill in the art will appreciate that prediction of these traits is useful in determining the end use of a bovine subject. For example, some bovine subjects may be better milk producers, while others may be better suited for meat production.

A trait is a characteristic of an organism that manifests itself in a phenotype. Many traits are the result of the expression of a single gene, but some are polygenic (i.e., result from simultaneous expression of more than one gene). A phenotype is an outward appearance or other visible characteristic of an organism. The bovine subject can be any bovine subject, for example a bull, a cow, a calf, a steer, or a heifer or any bovine embryo or tissue, and includes all breeds of bovines. For example, the animal can be a bovine subject ranging in age from conception to the time the animal is harvested.

The Examples below demonstrate that particular nucleotides present at the identified SNPs are predictive of traits or phenotypes of these traits in bovine subjects. In particular, the nucleotide at base position 669 of LDHB was predictive of calving rate, calf weight at birth, calf weight at weaning, calf height at weaning, milk butterfat concentration, breed lineage, susceptibility to fescue toxicosis, milk production, milk protein concentration, or milk somatic cell count. The nucleotide at base position 618 of LDHB was predictive of calf birth weight, calf weight at weaning, calf height at weaning, milk butterfat concentration, milk production, breed lineage, or calving rate. The nucleotide at base position 606 of LDHB was predictive of the milk butterfat concentration, milk somatic cell count, breed lineage, milk production, or milk protein concentration.

Polymorphisms in the LDHA coding sequence were also predictive of traits in a bovine subject. In particular, the nucleotide at base position 390 of LDHA was predictive of calving rate, prolactin concentration, calf birth weight, calf weight at weaning, calf height at weaning, breed lineage, serum LDH concentration, susceptibility to fescue toxicosis or milk production. The nucleotide at base position 530 of LDHA was predictive of the milk butterfat concentration, prolactin concentration, calf weight at weaning, calf height at weaning, breed lineage, serum LDH concentration, susceptibility to fescue toxicosis or calving rate.

Polymorphisms in the cytochrome P450 polynucleotide sequence were predictive of calf weight at weaning, calf height at weaning, milk butterfat concentration, breed lineage, milk production, milk protein concentration.

Polymorphisms in the prolactin promoter sequence were also predictive of traits in a bovine subject. In particular, the nucleotide at position −1286 of the prolactin promoter was predictive of the breed lineage, milk butterfat concentration, calving rate, or calf weight at weaning. The nucleotide at position −1161 of the prolactin promoter was predictive of calf weight at birth, calf weight at weaning, calf height at weaning, calving rate, breed lineage, milk protein concentration, milk somatic cell count or prolactin concentration.

Polymorphisms in the HSP70 promoter sequence were also predictive of traits in a bovine subject. In particular, the nucleotide at base position −895 of the HSP70 promoter was predictive of the date of calving, breed lineage and calving rate. The nucleotide at base position −1045 of the HSP70 promoter was predictive of body condition, breed lineage, serum prolactin concentration, hormone concentrations and nonesterified fatty acid concentration. The nucleotide at base position −1117 of the HSP70 promoter was predictive of body condition, breed lineage, prolactin concentration, hormone concentration and nonesterified fatty acid concentration. The nucleotide at base position −1125 of the HSP70 promoter was predictive of body condition, breed lineage, prolactin concentration, calving rate, hormone concentrations, LDH concentration and nonesterified fatty acid concentration. The nucleotide at base position −1128 of the HSP70 promoter was predictive of body condition, breed lineage, hormone concentration, calving rate and nonesterified fatty acid concentration. The nucleotide at base position −1134 of the HSP70 promoter was predictive of body condition, breed lineage, prolactin concentration, hormone concentration and nonesterified fatty acid concentration. The nucleotide at base position −1204 of the HSP70 promoter was predictive of body condition, breed lineage, hormone concentration and nonesterified fatty acid concentration.

Polymorphisms in the HSP70 coding sequence were also predictive of traits in a bovine subject. In particular, the nucleotide at base position 1851 of HSP70 was predictive of breed lineage. The nucleotides at base positions 1902, 1917, 1926 or 2098 of HSP70 were predictive of breed lineage, calf birth weight, calf weaning height, milk butterfat concentration and milk protein concentration. The nucleotide at base position 2033 of HSP-70 was predictive of calf weaning weight and milk somatic cell count. The nucleotide at base position 2087 of HSP70 was predictive of breed lineage.

The information used to predict the occurrence of the trait or the phenotype in an individual subject may be analyzed by any means available to those skilled in the art. Comparing the test subject to a number of subjects with a known nucleotide at the SNP site and a known phenotype of the trait allows prediction of the trait or phenotype in the test subject. In the Examples, a chi-squared analysis was performed. Those skilled in the art will appreciate that other statistical methods may be used to make predictions. Relationships between nucleotide occurrences of one or more SNPs and a trait can be identified using known statistical methods. A statistical analysis result which shows an association of one or more SNPs with a trait with at least 70%, 75%, 80%, 85%, 90%, 95%, 98%, or 99% confidence, or alternatively a probability of insignificance less than 0.10, less than 0.05 or less than 0.01, can be used to identify SNPs associated with a trait. These statistical tools may test for significance related to a null hypothesis that a SNP is not significantly different between groups with different traits. If the significance of this difference is low, it suggests the allele is not related to a trait.

In diploid organisms such as bovines, somatic cells include two alleles for each locus. The two alleles are referred to herein as a genotype or as a diploid pair, and the analysis of somatic cells, typically identifies the alleles for each copy of the gene. The methods provided herein include identifying a diploid pair of alleles. These alleles can be identical (homozygous) or can be different (heterozygous).

A sample useful for practicing the methods described herein can be any biological sample of a subject, typically a bovine subject. The sample contains nucleic acid molecules, including portions of the gene sequences to be examined, or corresponding encoded polypeptides, depending on the particular method used. The sample can be a cell, tissue or organ sample, or can be a sample of a biological material such as a body fluid, for example blood, milk, semen, saliva. A nucleic acid sample useful for practicing the methods provided herein may be DNA or RNA. The nucleic acid sample generally is a DNA sample, suitably genomic DNA. A cDNA sample or amplification product thereof can also be used. Where the SNPs are present in a coding region of a gene, the nucleic acid sample can be DNA or RNA, or products derived therefrom. Particular SNPs may be in coding regions of a gene and can result in polypeptides containing different amino acids at the positions corresponding to the SNPs due to a change to a codon encoding a distinct amino acid as demonstrated in the Examples. The methods described herein can also be practiced using a sample containing polypeptides of the subject.

Methods of the present invention can be used to predict more than one trait. For example, the methods can be used to predict a population or set of traits. The methods can be used to predict the breed, milk quantity and calving rate of a bovine subject. Such predictions can be made using one SNP or a multiple SNPs. Thus, a single SNP can be used to predict multiple traits, multiple SNPs can be used to predict a single trait or multiple traits and a single SNP can be used to predict a single trait. Where certain traits have either positive or negative correlations to each other, the methods allow identification of all SNPs that enhance or uncouple the correlation. In another aspect, the methods provide a system for determining the nucleotide occurrences at a population of bovine SNPs.

Any suitable method may be used to determine the nucleotide occurrence for a particular SNP in a sample, including any of numerous methods available to those of skill in the art. Such methods can utilize one or more oligonucleotide probes or primers, including, for example, an amplification primer pair that selectively hybridizes to a target polynucleotide that includes one or more of the associated bovine SNPs. Oligonucleotide probes useful in practicing the methods can include, for example, an oligonucleotide that is complementary to a portion of the target polynucleotide, including the position of the SNP, wherein the presence of a specific nucleotide at the position (i.e., the SNP) is detected by the presence or absence of selective hybridization of the probe. Such a method can include contacting the target polynucleotide and hybridized oligonucleotide with an endonuclease, and detecting the presence or absence of a cleavage product of the probe, depending on whether the nucleotide occurrence at the SNP site is complementary to the corresponding nucleotide of the probe.

An oligonucleotide ligation assay may be used to identify a nucleotide occurrence at a polymorphic position. In this assay a pair of probes that selectively hybridize upstream and adjacent to and downstream and adjacent to the site of the SNP are used. One of the probes includes a terminal nucleotide (3'-nucleotide) complementary to a nucleotide occurrence of the SNP. Where the terminal nucleotide of the probe is complementary to the nucleotide occurrence, selective hybridization includes the terminal nucleotide such that, in the presence of a ligase, the upstream and downstream oligonucleotides are ligated. The presence or absence of a ligation product is indicative of the nucleotide occurrence at the SNP site.

An oligonucleotide also can be useful as a primer, for example, for a primer extension reaction, wherein the product (or absence of a product) of the extension reaction is indicative of the nucleotide occurrence. In addition, a primer pair useful for amplifying (i.e. by PCR) a portion of the target polynucleotide including the SNP site can be useful. In this assay, the amplification product is examined to determine the nucleotide occurrence at the SNP site. Particularly useful methods include those that are readily adaptable to a high throughput format, to a multiplex format, or to both. The primer extension or amplification product can be detected directly or indirectly and/or can be sequenced using various methods known in the art. Amplification products which span a SNP locus can be sequenced using traditional sequence methodologies as in the Examples below. Alternatively, the products may be analyzed by RFLP analysis by treating the amplification products with restriction endonucleases which will differentially digest the products based on the nucleotide present at the SNP site.

Methods of the invention can identify nucleotide occurrences at SNPs using genome-wide sequencing or "microsequencing" methods. Whole-genome sequencing of individuals identifies all SNP genotypes in a single analysis. Microsequencing methods determine the identity of only a single nucleotide at a "predetermined" site. Such methods have particular utility in determining the presence and identity of SNPs in a target polynucleotide. Such microsequencing methods, as well as other methods for determining the nucleotide occurrence at a SNP locus are available to those skilled in the art.

The nucleotide present at a bovine SNP can also be identified using an immunoassay specific for one or more of the nucleotides at the SNP site. The bovine SNP can also be identified by contacting polynucleotides in the sample or polynucleotides derived from the sample, with a specific binding pair member that selectively hybridizes to a polynucleotide region comprising the bovine SNP, under conditions wherein the binding pair member specifically binds at or near the bovine SNP. The specific binding pair member can be an antibody or a complementary polynucleotide.

The nucleotide present at a SNP can be identified by other methods as well as those discussed above. For example, sequencing methods such as mass spectrometry, scanning electron microscopy, or methods in which a polynucleotide flows past a sorting device that can detect the sequence of the polynucleotide. The occurrence of a SNP can be identified using electrochemical detection devices as well. Other formats include melting curve analysis using fluorescently labeled hybridization probes, or intercalating dyes.

The methods of identifying the nucleotide present at a SNP may also utilize selective hybridization such as a microarray. Selective hybridization refers to hybridization under moderately stringent or highly stringent conditions such that a nucleotide sequence preferentially associates with a selected nucleotide sequence over unrelated nucleotide sequences to a large enough extent to be useful in identifying a nucleotide occurrence at a SNP. The nucleotide may be detected by comparing the amount of labeled oligonucleotide that binds to target nucleic acid molecule as compared to a nucleic acid molecule other than the target molecule, particularly a substantially similar (i.e., homologous) nucleic acid molecule other than the target nucleic acid molecule. Conditions that allow for selective hybridization can be determined empirically, or can be estimated based, for example, on the relative GC:AT content of the hybridizing oligonucleotide and the sequence to which it is to hybridize, the length of the hybridizing oligonucleotide, and the number of mismatches between the oligonucleotide and sequence to which it is to hybridize.

Methods of determining a nucleotide at a position that is correlated with expression of a trait in a bovine sample are also provided. The method includes detecting a target polynucleotide in a bovine sample using at least one oligonucleotide capable of binding to the target polynucleotide. The target polynucleotide includes a nucleotide at a position selected from the group consisting of 541 of LDHB, 606 of LDHB, 652 of LDHB, 669 of LDHB, 618 of LDHB, 390 of LDHA, 530 of LDHA, 994 of cytochrome P450, −1161 of the prolactin promoter, −1134 of the prolactin promoter, −1286 of the prolactin promoter, −895 of the HSP70 promoter, −1045 of the HSP70 promoter, −1069 of the HSP70 promoter, −1096 of the HSP70 promoter, −1117 of the HSP70 promoter, −1125 of the HSP70 promoter, −1128 of the HSP70 promoter, −1134 of the HSP70 promoter, −1154 of the HSP70 promoter, −1204 of the HSP70 promoter, 1851 of HSP70, 1899 of HSP70, 1902 of HSP70, 1917 of HSP70, 1926 of HSP70, 2033 of HSP70, 2087 of HSP70 and 2098 of HSP70. The identification of the nucleotide present at the SNP position in the bovine subject is determined. The identification of the nucleotide may be determined by analyzing the binding of the oligonucleotide to the target polynucleotide. Alternatively, the nucleotide may be determined by a variety of other means, including but not limited to, differential amplification, restriction fragment length polymorphism, DNA sequencing, primer extension, or DNA ligation as described above.

Also provided are methods of predicting the occurrence of a trait in a bovine subject. The method includes identifying a nucleotide of the bovine subject, wherein the nucleotide is selected from the group consisting of an adenine at position 541 of LDHB, a guanine at position 606 of LDHB, a thymine at position 652 of LDHB, a thymine at position 669 of LDHB, a guanine at position 618 of LDHB, an adenine at position 390 of LDHA, a cytosine at position 530 of LDHA, a cytosine at position 994 of cytochrome P450, a guanine at position −1161 of the prolactin promoter, a thymine at position −1286 of the prolactin promoter, a cytosine at position −895 of the HSP70 promoter, an adenine at position −1045 of the HSP70 promoter, a thymine at position −1069 of the HSP70 promoter, a guanine at position −1096 of the HSP70 promoter, an adenine at position −1117 of the HSP70 promoter, a cytosine at position −1125 of the HSP70 promoter, a thymine at position −1128 of the HSP70 promoter, a cytosine at position −1134 of the HSP70 promoter, a guanine at position −1154 of the HSP70 promoter, a cytosine at position −1204 of the HSP70 promoter, an adenine at position 1851 of HSP70, an adenine at position 1899 of HSP70, a thymine at position 1902 of HSP70, a thymine at position 1917 of HSP70, a guanine at position 1926 of HSP70, a cytosine at position 2033 of HSP70, a guanine at position 2087 of HSP70 and an adenine at position 2098 of HSP70. The identity of the nucleotide is indicative of and correlates to the occurrence of the trait or the phenotype expressed in the bovine subject.

Kits for determining the nucleotide present at a particular position within a bovine subject are also provided. The kits may be used to perform the methods described herein. The kits include a first oligonucleotide capable of binding to a target polynucleotide. The oligonucleotide may be used as a probe, primer or combined with a second oligonucleotide capable of binding the complement to the target polynucleotide to amplify the target polynucleotide. The target polynucleotide comprises a nucleotide at a position selected from the group consisting of 541 of LDHB, 606 of LDHB, 652 of LDHB, 669 of LDHB, 618 of LDHB, 390 of LDHA, 530 of LDHA, 994 of cytochrome P450, −1161 of the prolactin promoter, −1134 of the prolactin promoter, −1286 of the prolactin promoter, −895 of the HSP70 promoter, −1045 of the HSP70 promoter, −1069 of the HSP70 promoter, −1096 of the HSP70 promoter, −1117 of the HSP70 promoter, −1125 of the HSP70 promoter, −1128 of the HSP70 promoter, −1134 of the HSP70 promoter, −1154 of the HSP70 promoter, −1204 of the HSP70 promoter, 1851 of HSP70, 1899 of HSP70, 1902 of HSP70, 1917 of HSP70, 1926 of HSP70, 2033 of HSP70, 2087 of HSP70 and 2098 of HSP70. The target polynucleotides correspond to a portion of a bovine gene containing one or more SNP with a nucleotide associated with a bovine trait. In addition, the kits may contain reagents for performing methods described herein including, but not limited to, one or more detectable labels, which can be used to label a probe or primer or can be incorporated into a product generated using the probe or primer (e.g., an amplification product); one or more polymerases, which can be useful for a method that includes a primer extension or amplification procedure; or other enzyme or enzymes (e.g., a ligase or an endonuclease), which can be useful for performing an oligonucleotide ligation assay or a mismatch endonuclease cleavage assay; and/or one or more buffers or other reagents that are necessary to or can facilitate performing the methods. The primers or probes can be included in a kit in a labeled form, for example with a label such as biotin or an antibody. The kits may also include instructions for performing the method or for analyzing the results and making predictions based on the results.

In addition, polynucleotides encoding at least a portion of bovine LDH-B comprising an adenine at position 541, an adenine at position 606, a thymine at position 652, a thymine at position 669, a guanine at position 618 or a combination thereof are provided.

Polynucleotides encoding at least a portion of bovine LDH-A comprising an adenine at position 390, a cytosine at position 530 or a combination thereof are also provided.

A polynucleotide encoding at least a portion of bovine cytochrome P450 with a guanine at position 994 is also provided.

Polynucleotides are provided that encode at least a portion of the bovine prolactin promoter with a guanine at position −1161, a thymine at position −1286 relative to the prolactin start site or a combination thereof.

Polynucleotides are disclosed that encode at least a portion of the bovine HSP70 promoter comprising a nucleotide selected from the group consisting of a deletion of cytosine at position −895, an adenine at position −1045, a thymine at position −1069, a guanine at position −1096, an adenine at position −1117, a cytosine at position −1125, a thymine at position −1128, a cytosine at position −1134, a guanine at position −1154, a cytosine at position −1204 and a combination thereof, relative to the start site of HSP70.

Polynucleotides encoding at least a portion of bovine HSP70 are disclosed. These polynucleotides comprise a nucleotide selected from the group consisting of a deletion of adenine at position 1851, an adenine at position 1899, a thymine at position 1902, a thymine at position 1917, a guanine at position 1926, a cytosine at position 2033, a guanine at position 2087, an adenine at position 2098 and a combination thereof.

The Examples illustrate the various embodiments of the invention, but do not limit the scope of the attached claims.

EXAMPLES

Example 1

Single Nucleotide Polymorphisms within Bovine HSP-70 Gene

Methods and Materials

The genetic diversity of the HSP-70 gene between two different species of bovine was analyzed, the first species being more cold tolerant, *Bos taurus*, and the second species being more heat tolerant, *Bos indicus*. Genomic DNA was collected from 157 bovine subjects that were part of a long-term breeding program at the USDA-ARS Dale Bumpers Small Farms Research Center. The breed composition of the bovine subjects and the number of each breed used were as follows: *Bos taurus* (Angus; n=42), *Bos indicus* (Brahman; n=41), and *Bos taurus/Bos indicus* crosses (n=74). The crossbred bovine subjects were distributed as follows: 38 Angus sired Brahman dams, 36 Brahman sired Angus dams. The bovine subjects were *Bos taurus* (Angus; n=42), *Bos indicus* (Brahman; n=41), and *Bos taurus/Bos indicus* crosses (n=74). Blood samples were collected from the bovine subjects and the plasma was harvested.

DNA was extracted from the plasma and concentrated via ethanol precipitation. Primers HSP1778F (CGCTGGAGTCGTACGCCTTC) (SEQ ID NO:1) and HSP2326R (CTTGGAAGTAAACAGAAACGGG) (SEQ ID NO:2) were used to amplify a 548 base pair fragment from positions 1778 to 2326 of the polynucleotide encoding *Bos taurus*

HSP-70 (GenBank accession number U09861, SEQ ID NO:3). After amplification, primers HSP1803F (GAA-GAGCGCCGTGGAGGATG) (SEQ ID NO:4) and HSP2326R (SEQ ID NO:2) were used to sequence a 523 base pair fragment within the amplified region from positions 1803 to 2326 of SEQ ID NO:3.

Breed associations with each single nucleotide polymorphism (SNP) and the relationship between HSP-70 polymorphisms and milk composition, reproduction, and calf traits were determined using Chi-square analyses.

Results

Eight single nucleotide polymorphisms (SNPs) were identified. The SNPs were located at base position 1851 (n=7; 4.5%), 1899 (n=1; 0.64%), 1902 (n=6; 3.8%), 1917 (n=6; 3.8%), 1926 (n=6; 3.8%), 2033 (n=22; 14%), 2087 (n=10; 6.4%), and 2098 (n=6; 3.8%). The frequency and breed composition of each of the eight SNPs are summarized in Table 1. The base change, location, and effect on the amino acid are summarized in Table 2.

TABLE 1

Effects of breed composition[1] on SNP occurrence

| SNP | Sequence Position | Frequency[2] | AA | AB | BA | BB |
|---|---|---|---|---|---|---|
| 1 | 1851 | .045 | 2 | 0 | 5 | 0 |
| 2 | 1899 | .006 | 0 | 0 | 1 | 0 |
| 3 | 1902 | .038 | 0 | 1 | 1 | 4 |
| 4 | 1917 | .038 | 0 | 1 | 1 | 4 |
| 5 | 1926 | .038 | 0 | 1 | 1 | 4 |
| 6 | 2033 | .14 | 8 | 5 | 3 | 6 |
| 7 | 2087 | .064 | 0 | 2 | 2 | 6 |
| 8 | 2098 | .038 | 0 | 1 | 1 | 4 |

[1]The number of animals with the detected SNP by breed; AA-purebred Angus; AB-Angus sire; BA-Angus dam; BB-purebred Brahman
[2]Frequency of bovine subjects with that SNP in the population

TABLE 2

Relationship of SNP to potential codon position and translational products

| SNP | Base Change[1] | Codon Position[2] | Amino Acid Change |
|---|---|---|---|
| 1 (1851) | G to A | 3 | Ala (no change) |
| 2 (1899) | G to A | 3 | Leu (no change) |
| 3 (1902) | C to T | 3 | Asp (no change) |
| 4 (1917) | G to T | 3 | Ala (no change) |
| 5 (1926) | C to G | 3 | Asp to Glu |
| 6 (2033) | G to C | 2 | Gly to Ala |
| 7 (2087) | C to G | 2 | Post-translational |
| 8 (2098) | T to A | 1 | Post-translational |

[1]G-Guanine; A-Adenine; C-Cytosine; T-Thymine
[2]1-first base in codon; 2-second base in codon; 3-third base in codon SNP 1851 was found to be primarily related to Angus ancestry (P<0.11). SNPs 1902, 1917, 1926, 2087, and 2098 were found to be related to Brahman ancestry (P<0.11). SNP 2033 was not affected by breed (P>0.5) and SNP 1899 only occurred in one crossbred animal.

The SNPs at positions 1902, 1917, 1926, and 2098 appeared to be related. If one was present, they all were present. This was the case found in the genotype of six bovine subjects; four purebred Brahman, one Brahman/Angus, and one Angus/Brahman as stated in Table 1. These SNPs being consistently found together suggests a strong association to one another.

The SNP at position 2033 was the most predominate of the SNPs in number and also in identification from gel electrophoresis. The breed distribution found for the 22 bovine subjects displaying this SNP was evenly distributed among the four breed groups. This suggests that there is no breed interaction with the SNP.

The SNPs located at positions 2087 and 2098 are located after the stop codon (TAG) which ends at position 2082. A G/C SNP at position 2074, which is close to these two positions, in human HSP-70 was investigated by Wu et al. (2003) for an association with the risk of Parkinson's disease but no association was found with this particular SNP.

SEQ ID NO:3 that these samples were compared to is from the *Bos taurus* breed; therefore, the SNPs associated with our *Bos indicus* samples may represent subtle species differences in genetic coding and possibly give rise to future advances in the understanding of the ability of one breed to perform better in heat stress situations than another breed within a genus.

These results indicated that the HSP-70 gene in cattle is polymorphic, and most of the SNPs identified follow breed lineages. The relationship between HSP-70 polymorphisms and milk composition, reproduction, and calf traits are shown in Tables 3 and 4.

Cows with genotypes inconsistent with SEQ ID NO:3 at bases 1902, 1917, and 1926 had milk with a greater (P<0.05) percentage of butterfat and protein than other bovine subjects. Those same cows tended (P<0.1) to have calves that were taller than calves from non-SNP bovine subjects (Table 3). The birth weight of the cows containing the SNPs were also affected when the sex and forage conditions were considered. Heterozygous (GC) bovine subjects at base 2033 had fewer (P<0.05) somatic cells in their milk when compared with homozygous guanine bovine subjects. In addition, heterozygous bovine subjects grazing tall fescue had the lightest (P<0.1) calves at weaning (Table 4). Somatic cell counts were associated with the SNP at position 2033 which was the most prevalent in the HSP-70 segment and was equally distributed over breed groups. These results suggest that single nucleotide polymorphisms associated with heat shock protein 70 genes may serve as genetic markers for production and reproductive traits related to cattle profitability.

TABLE 3

Relationship between HSP-70 polymorphisms (c1902t, g1917t, and c1926g) and milk composition, reproduction, and calf traits.

| | Forage | | | | | |
|---|---|---|---|---|---|---|
| | Bermudagrass | | Tall Fescue | | | |
| | Genotype | | | | | |
| Item | CGC | TTG | CGC | TTG | SEM | Effects |
| Calvings, % | 84 | 83 | 80 | 89 | 9 | — |
| Prolactin, ng/ml | 87 | 83 | 23 | 11 | 28 | F |
| Milk | | | | | | |
| Volume, kg | 12.5 | 13.7 | 8.9 | 11.2 | 1.47 | f |
| Butterfat, % | 3.9 | 5.4 | 3.2 | 4.1 | 0.54 | G, F, |
| Protein, % | 3.2 | 3.8 | 3.4 | 3.5 | 0.12 | G, f * g |
| SCC, n | 301 | 637 | 215 | 63 | 180 | — |
| Calves | | | | | | |
| Birth wt, kg | 35.2 | 34.4 | 35.7 | 36.3 | 1.7 | F * G * S |
| Weaning wt, kg | 257 | 257 | 229 | 228 | 5 | A |
| Weaning ht, cm | 116.5 | 118.3 | 114.2 | 120.9 | 2.1 | g, A |

Effects: for the statistical model main effects were forage (F, f), genotype (G, g), age at weaning (A, a), sex of the calf (S, s), and month (M, m) in the case of multiple dates of collection. Uppercase letters indicate that the main effect was significant at a probability of less than 0.05; whereas, lowercase letters indicates a significance below 0.1. Interactions between main effects are indicated with an asterisk using the same uppercase and lowercase designations.

TABLE 4

Relationship between HSP-70 polymorphisms (g2033c) and milk composition, reproduction, and calf traits.

| | Forage | | | | | |
|---|---|---|---|---|---|---|
| | Bermudagrass | | Tall Fescue | | | |
| | Genotype | | | | | |
| Item | C | G | C | G | SEM | Effects |
| Calvings, % | 85 | 83 | 72 | 82 | 5.1 | — |
| Prolactin, ng/ml | 60 | 91 | 16 | 23 | 17 | F |
| Milk | | | | | | |
| Volume, kg | 13.0 | 12.5 | 8.2 | 9.2 | 0.83 | F |
| Butterfat, % | 4.1 | 3.9 | 2.9 | 3.3 | 0.24 | F |
| Protein, % | 3.2 | 3.3 | 3.5 | 3.4 | 0.07 | F |
| SCC, n | 175 | 350 | 47 | 259 | 103 | G |
| Calves | | | | | | |
| Birth wt, kg | 34.6 | 35.3 | 36.4 | 35.6 | 0.9 | s |
| Weaning wt, kg | 253 | 258 | 220 | 231 | 7.5 | F, S, f * g * s, A |
| Weaning ht, cm | 115.6 | 116.7 | 114 | 114.6 | 1.1 | f, S, A |

Effects: for the statistical model main effects were forage (F, f), genotype (G, g), age at weaning (A, a), sex of the calf (S, s), and month (M, m) in the case of multiple dates of collection. Uppercase letters indicate that the main effect was significant at a probability of less than 0.05; whereas, lowercase letters indicates a significance below 0.1. Interactions between main effects are indicated with an asterisk using the same uppercase and lowercase designations.

Example 2

Association of Single Nucleotide Polymorphisms in the Promoter Region of Bovine HSP-70 Gene with Body Condition and Pregnancy Rates in Brahman-Influenced Bovine Subjects Materials and Methods The relationships between single nucleotide polymorphisms located in the promoter region of bovine HSP-70 and body condition and calving rates were studied. Crossbred Brahman-influenced bovine subjects (n=103) were managed to achieve low or moderate body condition ("BC") at the initiation of the breeding season. Bovine subjects grazed stockpiled and spring-growth, endophyte-infected tall fescue (*Festuca arundinacea* Schreb.) pastures to obtain desired BC. Mean body condition score (BCS) of low (n=48) and moderate (n=55) BC bovine subjects was 4.3±0.1 and 6.0±0.1 (1=emaciated to 9=obese; Wagner et al., 1988), respectively.

Blood samples (plasma and serum) were collected from bovine subjects at −35 days before the breeding season. Samples were allowed to clot for 24 h at 4° C. (serum only), and centrifuged (1,500×g for 25 min.). Serum and plasma samples were stored at −20° C. until analysis; buffy coats were stored at −80° C. until analysis.

Genomic DNA was extracted from buffy coats using the QIAamp blood and body fluid spin protocol (QIAGEN, Valencia, Calif.), with slight modifications for increased yield, and the DNA purification from buffy coat prepared from 3 ml whole blood protocol (Puregene, Minneapolis, Minn.).

Primers HSP-Pro749F (GCCAGGAAACCAGAGA-CAGA, SEQ ID NO:5) and HSP-Pro 1268R (CCTACGCAG-GAGTAGGTGGT, SEQ ID NO:6) were used to PCR amplify and sequence a 539 base segment from base position 749 to 1288 in the promoter region of the *Bos taurus* Hsp70 gene (SEQ ID NO:7, GenBank accession number M98823). Sequences were analyzed and compared for sequence identity.

Quantitative traits including body condition, genotype (one SNP per analysis), and their interaction were analyzed by ANOVA. Dependent variables were Julian calving date, serum concentrations of GH, IGF-I, $T_3$, $T_4$, prolactin, NEFA, and Hsp70, and serum activities for LDH forward and LDH reverse. When F-tests for main effects were significant (P<0.05), multiple t-tests were performed for mean separation. For calving percentage a Chi-square analysis was performed with genotype, body condition, and their interactive effect tested.

Hormone concentrations were determined using validated RIA procedures. Serum concentrations of growth hormone (GH) were determined as reported by Hoefler and Hallford (1987) with an intra-assay CV of 8%. Insulin-like Growth Factor-I (IGF-I) serum concentrations were determined as described by Berrie et al (1995) with intra- and inter-assay CV of 12 and 16%, respectively. Triiodothyronine ($T_3$) serum concentrations were determined using Coat-A-Count Kits (Diagnostic Products Corp., Los Angeles, Calif.; Wells et al., 2003); intra- and inter-assay CV were 4 and 9% respectively. Serum concentrations of thyroxine ($T_4$) were determined using Coat-A-Count Kits (Richards et al., 1989) with intra- and inter-assay CV of 3 and 5%, respectively. Prolactin concentrations in serum were determined based on the procedures of Spoon and Hallford (1989); intra-assay CV was 7%. Plasma concentrations of nonesterified fatty acids (NEFA) were determined by an enzymatic calorimetric procedure (NEFA-C, Wako Chemicals, Inc., Dallas, Tex.) adapted for use in a 96-well microtiter plate system and expressed as microequivalents of palmitate per liter (Johnson and Peters, 1993). Lactate dehydrogenase (LDH) forward activity was measured by a kinetic calorimetric assay; intra- and inter-assay CV were 8 and 6%, respectively. Lactate dehydrogenase reverse activity was measured by a kinetic calorimetric assay; intra- and inter-assay CV were 6 and 17%, respectively. For measurements of LDH forward and reverse activity, individual samples ran in duplicate had CV not greater than 10%. Serum concentrations of Hsp70 were determined by a StressXpress Hsp70 ELISA Kit (Assay Designs, Ann Arbor, Mich.). Intra-assay CV was 3%.

Results

Nine single nucleotide polymorphisms (SNPs) [1045 (n=5, 4.9%), 1069 (n=4, 3.9%), 1096 (n=9, 8.7%), 1117 (n=7, 6.8%), 1125 (n=42, 40.8%), 1128 (n=36, 35%), 1134 (n=5, 4.9%), 1154 (n=8, 7.8%) and 1204 (n=31, 30.1%)] were found in the promoter region of the bovine Hsp70 gene. The deletion of a cytosine detected at base position 895. The base change and frequency of each SNP are summarized in Table 5.

TABLE 5

Base change and frequency of single nucleotide polymorphisms found in the promoter region of the bovine heat shock protein 70 gene.

| Base Position | Change | Frequency |
|---|---|---|
| 1045 | GG to AA | 0.0485 |
| 1069 | CC to TT | 0.0388 |
| 1096 | AA to GG | 0.0388 |
| | AA to AG | 0.0485 |
| 1117 | GG to AA | 0.0680 |
| 1125 | AA to CC | 0.3495 |
| | AA to AC | 0.0583 |
| 1128 | GG to TT | 0.3495 |
| 1134 | TT to CC | 0.0485 |
| 1154 | CC to CG | 0.0777 |
| 1204 | TT to CC | 0.3010 |
| 895 | -C | 0.1748 |

Table 6 presents the interactive means and effects for dependent variables at base position 1045. Bovine subjects with the AA genotype with low BC had greater (P<0.001) concentrations of $T_3$ than GG genotype bovine subjects with low BC (1.6 vs. 1.2 ng/mL) while no differences were found between AA and GG for bovine subjects with moderate BC. Serum concentrations of NEFA were influenced by genotype, body condition, and a genotype by BC interaction. Bovine subjects exhibiting low BC and homozygous for the SNP (AA) had greater (P<0.001) concentrations of NEFA than bovine subjects with low BC and the GG genotype, as well as bovine subjects with moderate BC of both genotypes (678 vs. 222, 234, and 234 mEq/L, respectively). Serum concentrations of prolactin were influenced by genotype. Bovine subjects that were homozygous for the SNP (AA) had greater (P<0.001) prolactin concentrations than GG genotype bovine subjects (35.5 vs. 11.4 ng/mL). Least squares means are in Table 6.

TABLE 6

Least squares means and standard errors (SEM) of dependent variables for base position 1045

| | Genotypes Observed[1] | | | | | |
|---|---|---|---|---|---|---|
| | GG | AA | GG | AA | | |
| | | | Body Condition | | | |
| | Moderate | | Low | | | |
| Dependent | | n | | | | |
| Variables[2] | 50 | 4 | 46 | 1 | SEM | Effect(s)[3,4] |
| Hsp70, ng/mL | 4.8 | 4.7 | 4.6 | 2.7 | 1.4 | — |
| Prolactin, ng/mL | 17.1 | 29.7 | 5.6 | 41.3 | 5.6 | G* |
| GH, ng/mL | 6.5 | 5.4 | 5.8 | 7.0 | 2.3 | — |
| IGF-1, ng/mL | 94.0 | 90.5 | 69.8 | 73.0 | 13.9 | — |
| $T_3$, ng/mL | 1.4[a] | 1.3[a] | 1.2[b] | 1.6[a] | 0.1 | G × BC* |
| $T_4$, ng/mL | 41.1 | 39.9 | 43.5 | 43.8 | 3.4 | — |
| NEFA, mEq/L | 234[b] | 234[b] | 222[b] | 678[a] | 42 | G***, BC***, G × BC*** |
| LDH (f), IU/mg | 7.7 | 7.4 | 8.0 | 8.8 | 0.6 | — |
| LDH (r), IU/mg | 2.2 | 2.4 | 2.3 | 2.4 | 0.3 | — |
| Calving Date | 77 | 71 | 79 | 62 | 10.9 | — |
| Calving Rate[5], % | 72 (36/50) | 100 (4/4) | 59 (27/46) | 100 (1/1) | | p = 0.21 |

[1]Heterozygous genotype was omitted as it was not representative of the population
[2]Heat Shock Protein = Hsp70; Growth Hormone = GH; Insulin-like Growth Factor = IGF; Triiodothyronine = $T_3$; Thyroxine = $T_4$; Nonesterified fatty acid = NEFA; Lactate Dehydrogenase = LDH [(f) = forward; (r) = reverse]
[3]G = genotype; BC = body condition; G × BC = interaction
[4]*P < 0.05, P < 0.01, *P < 0.001
[5]Number of observations in parentheses; calving rate was number of bovine subjects that calved divided by total number of bovine subjects in group
[a,b]Within a row, means without a common superscript differ (P < 0.05)

Table 7 presents the interactive means and effects for dependent variables at base position 1069. Serum concentrations of $T_3$ tended (P<0.10) to be influenced by body condition. Bovine subjects exhibiting moderate BC had greater (P<0.10) concentrations of $T_3$ than bovine subjects exhibiting low BC (1.5 vs. 1.3 ng/mL). Serum concentrations of $T_4$ were influenced by BC, with bovine subjects classified as low having greater (P<0.05) concentrations than bovine subjects classified as moderate (46 vs. 39 ng/mL).

TABLE 7

Least squares means and standard errors (SEM) of dependent variables for base position 1069

| | Genotypes Observed[1] | | | | | |
|---|---|---|---|---|---|---|
| | CC | TT | CC | TT | | |
| | | | Body Condition | | | |
| | Moderate | | Low | | | |
| Dependent | | n | | | | |
| Variable[2] | 52 | 2 | 45 | 2 | SEM | Effect(s)[3,4] |
| Hsp70, ng/mL | 4.8 | 3.3 | 4.7 | 12.3 | 1.2 | — |
| Prolactin, ng/mL | 18.5 | 14.0 | 5.9 | 19.5 | 5.7 | — |
| GH, ng/mL | 6.4 | 6.1 | 5.8 | 5.0 | 3.1 | — |
| IGF-1, ng/mL | 92.8 | 110.5 | 69.7 | 76.0 | 15.4 | — |
| $T_3$, ng/mL | 1.4 | 1.6 | 1.1 | 1.4 | 0.1 | BC† |
| $T_4$, ng/mL | 41.2 | 36.3 | 43.2 | 49.6 | 3.2 | BC* |
| NEFA, mEq/L | 234 | 222 | 231 | 267 | 45 | — |
| LDH (f), IU/mg | 7.7 | 7.9 | 8.1 | 8.4 | 0.6 | — |
| LDH (r), IU/mg | 2.2 | 2.5 | 2.3 | 2.1 | 0.3 | — |
| Julian Calving Date | 77 | 58 | 79 | 90 | 7.6 | — |
| Calving Rate[5], % | 75 (39/52) | 100 (2/2) | 58 (26/45) | 100 (2/2) | | p = 0.16 |

[1]Heterozygous genotype was omitted as it was not representative of the population
[2]Heat Shock Protein = Hsp70; Growth Hormone = GH; Insulin-like Growth Factor = IGF; Triiodothyronine = $T_3$; Thyroxine = $T_4$; Nonesterified fatty acid = NEFA; Lactate Dehydrogenase = LDH [(f) = forward; (r) = reverse]
[3]G = genotype; BC = body condition; G × BC = interaction
[4]†P < 0.10, *P < 0.05, P < 0.01, *P < 0.001
[5]Number of observations in parentheses; calving rate was number of bovine subjects that calved divided by total number of bovine subjects in group.

Table 8 presents the interactive means and effects for dependent variables at base position 1096. Bovine subjects with moderate body condition had higher (P<0.05) serum concentrations of $T_3$ than bovine subjects with low BC (1.4 vs. 1.1 ng/mL). Serum concentrations of LDH reverse activity was greater (P<0.05) for bovine subjects with low BC than bovine subjects with moderate BC (2.8 vs. 2.2 IU/mg).

TABLE 8

Least squares means and standard errors (SEM) of dependent variables for base position 1096

| | Genotypes Observed | | | | | | | |
|---|---|---|---|---|---|---|---|---|
| | AA | AG | GG | AA | AG | GG | | |
| | | | Body Condition | | | | | |
| | Moderate | | | Low | | | | |
| Dependent | | | n | | | | | |
| Variable[1] | 48 | 4 | 3 | 46 | 1 | 1 | SEM | Effect(s)[2,3] |
| Hsp70, ng/mL | 4.5 | 5.5 | 3.5 | 4.5 | 1.2 | 6.2 | 1.7 | — |

TABLE 8-continued

Least squares means and standard errors (SEM) of dependent variables for base position 1096

| | Genotypes Observed | | | | | | | |
|---|---|---|---|---|---|---|---|---|
| | AA | AG | GG | AA | AG | GG | | |
| | | | Body Condition | | | | | |
| | Moderate | | | Low | | | | |
| Dependent | | | n | | | | | |
| Variable[1] | 48 | 4 | 3 | 46 | 1 | 1 | SEM | Effect(s)[2,3] |
| Prolactin, ng/mL | 18.8 | 12.8 | 13.8 | 6.8 | 4.4 | 1.0 | 7.5 | — |
| GH, ng/mL | 6.6 | 4.1 | 4.4 | 5.9 | 4.7 | 3.4 | 3.4 | — |
| IGF-1, ng/mL | 96.3 | 68.7 | 72.7 | 72.2 | 54.0 | 47.0 | 17.3 | — |
| $T_3$, ng/mL | 1.4 | 1.3 | 1.4 | 1.2 | 1.1 | 1.0 | 0.1 | BC* |
| $T_4$, ng/mL | 40.9 | 40.6 | 39.9 | 43.5 | 45.3 | 52.9 | 4.6 | — |
| NEFA, mEq/L | 241 | 242 | 186 | 234 | 429 | 177 | 60 | — |
| LDH (f), IU/mg | 7.6 | 7.9 | 8.6 | 7.8 | 10.2 | 8.9 | 0.8 | — |
| LDH(r), IU/mg | 2.3 | 2.0 | 2.3 | 2.2 | 2.4 | 3.7 | 0.3 | BC* |
| Julian Calving Date | 76 | 78 | 75 | 80 | 77 | 76 | 10.2 | — |
| Calving Rate[4], % | 73 (35/48) | 75 (3/4) | 100 (3/3) | 59 (27/46) | 100 (1/1) | 100 (1/1) | p = 0.44 | |

[1]Heat Shock Protein = Hsp70; Growth Hormone = GH; Insulin-like Growth Factor = IGF; Triiodothyronine = $T_3$; Thyroxine = $T_4$; Nonesterified fatty acid = NEFA; Lactate Dehydrogenase = LDH [(f) = forward; (r) = reverse]
[2]G = genotype; B = body condition; G × B = interaction
[3]*P < 0.05, P < 0.01, *P < 0.001
[4]Number of observations in parentheses; calving rate was number of bovine subjects that calved divided by total number of bovine subjects in group.

Table 9 presents the interactive means and effects for dependent variables at base position 1117. Concentrations of $T_3$ were greater (P<0.05) in bovine subjects exhibiting a base change from guanine to adenine with low BC than homozygous guanine bovine subjects with low body condition (1.4 vs. 1.1 ng/mL), while there was no difference between mean $T_3$ concentrations in moderate BC bovine subjects (interaction, p<0.05). Concentrations of NEFA were influenced by a genotype×BC interaction. Bovine subjects with the AA genotype with low BC had greater (P<0.05) circulating concentrations of NEFA than GG genotype bovine subject exhibiting the same body condition (404 vs. 220 mEq/L), while no difference was observed in moderate BC bovine subjects (interaction, p<0.05). Prolactin concentrations were greater (P<0.05) in bovine subjects with the SNP (guanine to adenine) than homozygous G bovine subjects (23.5 vs. 11.4 ng/mL).

TABLE 9

Least squares means and standard errors (SEM) of dependent variables for base position 1117.

| | Genotypes Observed[1] | | | | | |
|---|---|---|---|---|---|---|
| | GG | AA | GG | AA | | |
| | | | Body Condition | | | |
| | Moderate | | Low | | | |
| Dependent | | | n | | | |
| Variable[2] | 50 | 14 | 44 | 3 | SEM | Effect(s)[3,4] |
| Hsp70, ng/mL | 4.7 | 4.7 | 4.8 | 2.2 | 1.1 | — |
| Prolactin, ng/mL | 17.9 | 22.4 | 5.1 | 24.5 | 4.6 | G* |
| GH, ng/mL | 6.5 | 5.5 | 5.8 | 6.3 | 2.3 | — |
| IGF-1, ng/mL | 93.7 | 93.3 | 70.0 | 68.0 | 11.7 | — |
| $T_3$, ng/mL | 1.4[a] | 1.4[a] | 1.1[b] | 1.4[a] | 0.1 | G × BC* |
| $T_4$, ng/mL | 41.2 | 38.2 | 43.5 | 44.0 | 2.7 | — |
| NEFA, mEq/L | 232[b] | 260[ab] | 220[b] | 404[a] | 34 | G**, G × BC* |
| LDH (f), IU/mg | 7.7 | 7.8 | 8.1 | 8.1 | 0.5 | — |
| LDH (r), IU/mg | 2.2 | 2.5 | 2.3 | 2.4 | 0.2 | — |
| Julian Calving Date | 78 | 63 | 81 | 64 | 6.5 | — |
| Calving Rate[5], % | 74 (37/50) | 100 (4/4) | 59 (26/44) | 67 (2/3) | p = 0.23 | |

[1]Heterozygous genotype was omitted as it was not representative of the population
[2]Heat Shock Protein = Hsp70; Growth Hormone = GH; Insulin-like Growth Factor = IGF; Triiodothyronine = $T_3$; Thyroxine = $T_4$; Nonesterified fatty acid = NEFA; Lactate Dehydrogenase = LDH 4[(f) = forward; (r) = reverse]
[3]G = genotype; BC = body condition; G × BC = interaction
[4]*P < 0.05, P < 0.01, *P < 0.001
[5]Number of observations in parentheses; calving rate was number of bovine subjects that calved divided by total number of bovine subjects in group
[ab]Within a row, means without a common superscript differ (P < 0.05)

Table 10 presents the interactive means and effects for dependent variables at base position 1125. At base position 1125, moderate BC bovine subjects had greater (P<0.05)

concentrations of $T_3$ than bovine subjects with low BC (1.4 vs. 1.2 ng/mL). Bovine subjects with moderate BC had greater (P<0.05) concentrations of prolactin than bovine subjects with low BC (16.7 vs. 6.6 ng/mL). IGF-I concentrations were greater (P<0.05) for moderate BC bovine subjects than bovine subjects classified as low BC (90 vs. 71 ng/mL). Serum concentrations of LDH forward activity were influenced by a genotype×BC interaction. Heterozygous, low BC bovine subjects had the lowest (P<0.01) activity of LDH forward of all genotype×BC groups although not statistically different from heterozygous moderate BC bovine subjects. Lactate dehydrogenase reverse serum activity had a similar interaction; heterozygous, low BC bovine subjects had the lowest (P<0.05) activity of all genotype×BC groups although not statistically different from moderate AA and AC or low BC bovine subjects. Bovine subjects that were homozygous CC at base position 1125 calved earlier than homozygous AA and heterozygous bovine subjects (75 vs. 79, 77 days, respectively). Calving rate was higher (P<0.01) for bovine subjects that were homozygous AA at the 1125 site. Bovine subjects with moderate body condition and AA at base position 1125 tended to have higher (P<0.10) pregnancy rates than AA genotype bovine subjects with low BC. Bovine subjects that were homozygous for the SNP (CC) with low BC had the lowest pregnancy rate of all genotypes and BC groups. There was no change in pregnancy rates for heterozygous bovine subjects based on body condition.

TABLE 10

Least squares means and standard errors (SEM) of dependent variables for base position 1125.

| | Genotypes Observed | | | | | | | |
|---|---|---|---|---|---|---|---|---|
| | AA | AC | CC | AA | AC | CC | | |
| | Body Condition | | | | | | | |
| | Moderate | | | Low | | | | |
| Dependent | | | n | | | | | |
| Variable[1] | 30 | 3 | 22 | 31 | 3 | 14 | SEM | Effect(s)[2,3] |
| Hsp70, ng/mL | 5.3 | 1.6 | 4.1 | 4.6 | 3.4 | 4.6 | 1.0 | — |
| Prolactin, ng/mL | 19.6 | 13.9 | 16.5 | 6.6 | 6.8 | 6.4 | 4.5 | BC* |
| GH, ng/mL | 1.2 | 5.1 | 8.6 | 6.0 | 5.9 | 5.2 | 2.0 | — |
| IGF-1, ng/mL | 90.1 | 81.3 | 97.8 | 74.9 | 76.3 | 61.8 | | BC* |
| $T_3$, ng/mL | 1.4 | 1.3 | 1.4 | 1.2 | 1.2 | 1.2 | 0.1 | BC* |
| $T_4$, ng/mL | 42.1 | 38.5 | 39.6 | 43.7 | 38.9 | 45.0 | 2.6 | — |
| NEFA, mEq/L | 246 | 281 | 219 | 243 | 235 | 223 | 36 | — |
| LDH (f), IU/mg | 7.8$^a$ | 7.9$^{ab}$ | 7.5$^a$ | 7.9$^a$ | 5.6$^b$ | 8.3$^a$ | 0.5 | G × BC** |
| LDH (r), IU/mg | 2.3$^{abc}$ | 2.6$^{abc}$ | 2.1$^b$ | 2.2$^{abc}$ | 1.7$^c$ | 2.5$^a$ | 0.2 | G × BC* |
| Julian Calving Date | 79 | 76 | 71 | 80 | 78 | 78 | 7.3 | — |
| Calving rate[4], % | 83 (25/30) | 67 (2/3) | 64 (14/22) | 71 (22/31) | 67 (2/3) | 36 (5/14) | | p = 0.07 |

[1]Heat Shock Protein = Hsp70; Growth Hormone = GH; Insulin-like Growth Factor = IGF; Triiodothyronine = $T_3$; Thyroxine = $T_4$; Nonesterified fatty acid = NEFA; Lactate Dehydrogenase = LDH [(f) = forward; (r) = reverse]
[2]G = genotype; BC = body condition; G × BC interaction
[3]*P < 0.05, P < 0.01, *P < 0.001
[4]Number of observations in parentheses; calving rate was number of bovine subjects that calved divided by total number of bovine subjects in group
$^{abc}$Within a row, means without a common superscript differ (P < 0.05)

Table 11 presents the interactive means and effects for dependent variables at base position 1128. Prolactin concentrations were greater (P<0.001) for moderate BC bovine subjects than low BC bovine subjects (18.3 vs. 5.7 ng/mL). Bovine subjects with moderate BC had greater (P<0.01) concentrations of IGF-I than bovine subjects with low BC (93.8 vs. 66.4 ng/mL). Lactate dehydrogenase reverse activity was influenced by a genotype×BC interaction. Bovine subjects that were homozygous for the SNP (guanine to thymine) with low body condition had greater (P<0.05) concentrations of LDH reverse activity than GG genotype bovine subjects with low body condition (2.6 vs. 2.2 IU/mg). Bovine subjects that expressed a base change of guanine to thymine at base position 1128 calved later than GG genotype bovine subjects (81 vs. 78 days). Calving rate was higher (P<0.01) for bovine subjects exhibiting the GG genotype at base position 1128. Bovine subjects homozygous for the SNP (guanine to thymine) with low BC had the lowest pregnancy rate of all genotypes and BC groups.

TABLE 11

Least squares means and standard errors (SEM) of dependent variables for base position 1128.

| | Genotypes Observed[1] | | | | | |
|---|---|---|---|---|---|---|
| | GG | TT | GG | TT | | |
| | | | Body Condition | | | |
| | Moderate | | Low | | | |
| | n | | | | | |
| Dependent Variable[2] | 29 | 24 | 35 | 12 | SEM | Effect(s)[3,4] |
| Hsp70, ng/mL | 5.3 | 4.1 | 4.5 | 4.8 | 0.6 | — |
| Prolactin, ng/mL | 18.1 | 18.5 | 7.4 | 4.1 | 3.0 | BC** |
| GH, ng/mL | 5.2 | 7.7 | 6.0 | 5.1 | 1.5 | — |
| IGF-1, ng/mL | 98.3 | 89.2 | 74.2 | 58.7 | 6.8 | BC** |
| $T_3$, ng/mL | 1.5 | 1.4 | 1.2 | 1.1 | 0.1 | — |
| $T_4$, ng/mL | 41.9 | 40.0 | 43.5 | 43.4 | 1.7 | — |
| NEFA, mEq/L | 242 | 226 | 236 | 222 | 18 | — |
| LDH (f), IU/mg | 7.7 | 7.7 | 8.0 | 8.2 | 0.3 | — |
| LDH (r), IU/mg | $2.3^{ab}$ | $2.1^b$ | $2.2^b$ | $2.6^a$ | 0.1 | G × BC* |
| Julian Calving Date | 78 | 74 | 79 | 89 | 5.3 | — |
| Calving Rate[5], % | 79 | 67 | 74 | 25 | | p = 0.006 |
| | (23/29) | (16/24) | (26/35) | (3/12) | | |

[1]Heterozygous genotype was omitted as it was not representative of the population
[2]Heat Shock Protein = Hsp70; Growth Hormone = GH; Insulin-like Growth Factor = IGF; Triiodothyronine = $T_3$; Thyroxine = $T_4$; Nonesterified fatty acid = NEFA; Lactate Dehydrogenase = LDH [(f) = forward; (r) = reverse]
[3]G = genotype; BC = body condition; G × BC = interaction
[4]*P < 0.05, P < 0.01, *P < 0.001
[5]Number of observations in parentheses; calving rate was number of bovine subjects that calved divided by total number of bovine subjects in group
$^{ab}$Within a row, means without a common superscript differ (P < 0.05)

Table 12 presents the interactive means and effects for dependent variables at base position 1134. Moderate BC bovine subjects with the SNP (thymine to cytosine) had greater (P<0.001) concentrations of $T_3$ than TT bovine subjects with low BC (1.4 vs. 1.2 ng/mL). Bovine subjects with the CC genotype and low BC had greater (P<0.001) concentrations of $T_3$ than TT genotype bovine subjects with low BC (1.6 vs. 1.2 ng/mL). Serum concentrations of NEFA were influenced by a genotype×BC interaction at base position 1134. Bovine subjects classified as low BC had greater (P<0.001) NEFA concentrations than bovine subjects classified as moderate BC (453 vs. 235 mEq/L). Bovine subjects with the CC genotype with low BC had a higher p<0.05) amount of circulating NEFA than any other group. Bovine subjects with the CC genotype had greater (P<0.001) concentrations of prolactin than bovine subjects with the SNP (TT; 36 vs. 11 ng/mL).

TABLE 12

Least squares means and standard errors (SEM) of dependent variables for base position 1134.

| | Genotypes Observed | | | | | |
|---|---|---|---|---|---|---|
| | TT | CC | TT | CC | | |
| | | | Body Condition | | | |
| | Moderate | | Low | | | |
| | n | | | | | |
| Dependent Variable[1] | 51 | 4 | 47 | 1 | SEM | Effect(s)[2,3] |
| Hsp70, ng/mL | 4.6 | 4.2 | 4.5 | 2.7 | 1.3 | — |
| Prolactin, ng/mL | 16.9 | 30.4 | 5.8 | 41.3 | 5.6 | G* |
| GH, ng/mL | 6.5 | 4.2 | 5.8 | 7.0 | 2.7 | — |
| IGF-1, ng/mL | 92.9 | 93.5 | 71.3 | 73.0 | 13.7 | — |
| $T_3$, ng/mL | $1.4^a$ | $1.3^{ab}$ | $1.2^b$ | $1.6^a$ | 0.1 | G × BC** |
| $T_4$, ng/mL | 41.0 | 38.6 | 43.8 | 43.8 | 3.4 | — |
| NEFA, mEq/L | $238^b$ | $232^b$ | $228^b$ | $678^a$ | 44 | G**, BC**, G × BC** |
| LDH (f), IU/mg | 7.7 | 7.5 | 7.9 | 8.8 | 0.6 | — |

TABLE 12-continued

Least squares means and standard errors (SEM) of dependent variables for base position 1134.

| | Genotypes Observed | | | | | |
|---|---|---|---|---|---|---|
| | TT | CC | TT | CC | | |
| | | | Body Condition | | | |
| | Moderate | | Low | | | |
| | | n | | | | |
| Dependent Variable[1] | 51 | 4 | 47 | 1 | SEM | Effect(s)[2,3] |
| LDH (r), IU/mg | 2.2 | 2.2 | 2.3 | 2.4 | 0.3 | — |
| Julian Calving Date | 77 | 70 | 80 | 62 | 7.9 | — |
| Calving Rate[4], % | 73 | 100 | 60 | 100 | | p = 0.22 |
| | (37/51) | (4/4) | (28/47) | (1/1) | | |

[1]Heat Shock Protein = Hsp70; Growth Hormone = GH; Insulin-like Growth Factor = IGF; Triiodothyronine = $T_3$; Thyroxine = $T_4$; Nonesterified fatty acid = NEFA; Lactate Dehydrogenase = LDH [(f) = forward; (r) = reverse]
[2]G = genotype; BC = body condition; G × BC = interaction
[3]*$P < 0.05$, $P < 0.01$, *$P < 0.001$
[4]Number of observations in parentheses; calving rate was number of bovine subjects that calved divided by total number of bovine subjects in group
[a,b] Within a row, means without a common superscript differ ($P < 0.05$)

Table 13 presents the interactive means and effects for dependent variables at base position 1154. Serum concentrations of $T_3$ were greater ($P < 0.05$) for bovine subjects classified with moderate body condition than bovine subjects having low body condition (1.4 vs. 1.2 ng/mL). Similarly, concentrations of IGF-I were greater ($P < 0.05$) for bovine subjects classified as having moderate body condition than those having low body condition (89.6 vs. 60.2 ng/mL). Bovine subjects classified as having low body condition had greater ($P < 0.05$) concentrations of LDH forward activity than bovine subjects classified as moderate (8.5 vs. 7.4 IU/mg).

TABLE 13

Least squares means and standard errors (SEM) of dependent variables for base position 1154

| | Genotypes Observed[1] | | | | | |
|---|---|---|---|---|---|---|
| | CC | CG | CC | CG | | |
| | | | Body Condition | | | |
| | Moderate | | Low | | | |
| Dependent | | n | | | | |
| Variable[2] | 49 | 5 | 45 | 3 | SEM | Effect(s)[3,4] |
| Hsp70, ng/mL | 4.7 | 4.9 | 4.8 | 2.2 | 1.0 | — |
| Prolactin, ng/mL | 19.0 | 13.3 | 6.0 | 12.2 | 4.5 | — |
| Growth Hormone | 6.5 | 5.5 | 5.8 | 5.4 | 2.4 | — |
| IGF-1, ng/mL | 95.1 | 84.0 | 70.9 | 49.5 | 11.6 | BC* |
| $T_3$, ng/mL | 1.4 | 1.3 | 1.2 | 1.3 | 0.1 | BC* |
| $T_4$, ng/mL | 41.0 | 41.1 | 43.1 | 49.0 | 2.6 | — |
| NEFA, mEq/L | 240 | 184 | 228 | 290 | 34 | — |
| LDH (f), IU/mg | 7.7 | 7.2 | 8.0 | 8.9 | 0.5 | BC* |
| LDH (r), IU/mg | 2.3 | 1.8 | 2.3 | 2.4 | 0.2 | — |

TABLE 13-continued

Least squares means and standard errors (SEM) of dependent variables for base position 1154

| | Genotypes Observed[1] | | | | | |
|---|---|---|---|---|---|---|
| | CC | CG | CC | CG | | |
| | | | Body Condition | | | |
| | Moderate | | Low | | | |
| Dependent | | n | | | | |
| Variable[2] | 49 | 5 | 45 | 3 | SEM | Effect(s)[3,4] |
| Julian Calving Date | 76 | 77 | 81 | 71 | 6.2 | — |
| Calving Rate[5], % | 73 | 80 | 58 | 100 | | p = 0.21 |
| | (36/49) | (4/5) | (26/45) | (3/3) | | |

[1]Homozygous GG animals were omitted because they were not representative of a population
[2]Heat Shock Protein = Hsp70; Growth Hormone = GH; Insulin-like Growth Factor = IGF; Triiodothyronine = $T_3$; Thyroxine = $T_4$; Nonesterified fatty acid = NEFA; Lactate Dehydrogenase = LDH [(f) = forward; (r) = reverse]
[3]G = genotype; BC = body condition; G × BC = interaction
[4]*$P < 0.05$, $P < 0.01$, *$P < 0.001$
[5]Number of observations in parentheses; calving rate was number of bovine subjects that calved divided by total number of bovine subjects in group.

Table 14 presents the interactive means and effects for dependent variables at position 1204. Bovine subjects classified with moderate body condition had greater ($P < 0.001$) concentrations of $T_3$ than bovine subjects classified with low body condition (1.4 vs. 1.2 ng/mL). Serum concentrations of NEFA were influenced by genotype; bovine subjects with the SNP (CC) had higher ($P < 0.05$) concentrations than homozygous TT bovine subjects (268 vs. 218 mEq/L). Concentrations of prolactin were greater ($P < 0.001$) in moderate body condition bovine subjects than low body condition bovine subjects (18.2 vs. 7.2 ng/mL). In addition, moderate BC bovine subjects had greater ($P < 0.01$) concentrations of IGF-I than low BC bovine subjects (93.5 vs. 71.2 ng/mL). A genotype×BC interaction ($p < 0.05$) was observed for LDH forward activity. Bovine subjects with CC genotype had higher values than TT in low BC bovine subjects, but no difference was observed in moderate BC bovine subjects.

TABLE 14

Least squares means and standard error means (SEM) of dependent variables for base position 1204

| | Genotypes Observed[1] | | | | | |
|---|---|---|---|---|---|---|
| | TT | CC | TT | CC | | |
| | | | Body Condition | | | |
| | Moderate | | Low | | | |
| | n | | | | | |
| Dependent Variable[2] | 33 | 22 | 36 | 9 | SEM | Effect(s)[3,4] |
| Hsp70, ng/mL | 4.9 | 4.4 | 4.5 | 5.7 | 0.7 | — |
| Prolactin, ng/mL | 18.7 | 17.8 | 4.9 | 9.5 | 3.2 | BC** |
| Growth Hormone | 5.1 | 8.6 | 5.9 | 5.3 | 1.6 | — |
| IGF-1, ng/mL | 96.6 | 90.5 | 68.2 | 74.1 | 7.3 | BC** |
| $T_3$, ng/mL | 1.5 | 1.4 | 1.1 | 1.2 | 0.1 | BC** |
| $T_4$, ng/mL | 41.1 | 40.9 | 42.8 | 44.4 | 1.8 | — |
| NEFA, mEq/L | 220 | 252 | 216 | 284 | 24 | G* |
| LDH (f), IU/mg | 7.9[b] | 7.3[b] | 7.8[b] | 8.6[a] | 0.3 | BC*, G × BC* |
| LDH (r), IU/mg | 2.3 | 2.1 | 2.2 | 2.5 | 0.1 | — |
| Julian Calving Date | 78 | 73 | 79 | 88 | 4.7 | — |
| Calving Rate[5], % | 72 | 77 | 61 | 56 | | p = 0.45 |

[1]Heterzygous genotype was omitted as it was not representative of the population
[2]Heat Shock Protein = Hsp70; Growth Hormone = GH; Insulin-like Growth Factor = IGF; Triiodothyronine = $T_3$; Thyroxine = $T_4$; Nonesterified fatty acid = NEFA; Lactate Dehydrogenase = LDH [(f) = forward; (r) = reverse]
[3]G = genotype; BC = body condition; G × BC = interaction
[4]*P < 0.05, P < 0.01, *P < 0.001
[5]Number of observations in parentheses; calving rate was number of bovine subjects that calved divided by total number of bovine subjects in group
[a,b]Within a row, means without a common superscript differ (P < 0.05)

Table 15 presents the interactive means and effects for dependent variables for deletion of cytosine at base position 895. Serum concentrations of $T_4$ were greater (P<0.05) in bovine subjects with low BC than bovine subjects with moderate BC (44 vs. 39 ng/mL), while bovine subjects with moderate BC had greater (P<0.001) concentrations of $T_3$ than bovine subjects with low BC (1.4 vs. 1.2 ng/mL). Prolactin concentrations were greater (P<0.01) for bovine subjects with moderate BC than bovine subjects with low BC (17 vs. 6 ng/mL). Similarly, IGF-I concentrations were greater (P<0.05) in moderate BC bovine subjects than low BC bovine subjects (86 vs. 69 ng/mL). Bovine subjects with the deletion (C-) at base position 895 calved significantly later (P<0.001) than bovine subjects without the deletion (CC) (101 vs. 79 days). Bovine subjects that did not exhibit the deletion (CC) had higher (P<0.001) calving rates than bovine subjects with the deletion (C-). Low body condition bovine subjects with the deletion (C-) had the lowest calving rate of all genotypes and BC groups.

TABLE 15

Least squares means and standard error means (SEM) of dependent variables and calving rates for base position 895

| | Genotypes Observed[1] | | | | | |
|---|---|---|---|---|---|---|
| | CC | C- | CC | C- | | |
| | | | Body Condition | | | |
| | Moderate | | Low | | | |
| Dependent Variable[2] | n | | | | | |
| | 48 | 7 | 37 | 11 | SEM | Effect(s)[3,4] |
| Hsp70, ng/mL | 4.5 | 5.1 | 4.6 | 3.9 | 0.8 | — |
| Prolactin, ng/mL | 18.2 | 16.7 | 7.1 | 5.0 | 3.4 | BC** |
| Growth Hormone | 6.5 | 4.6 | 5.9 | 5.4 | 1.7 | — |
| IGF-1, ng/mL | 95.4 | 76.2 | 73.7 | 63.7 | 7.8 | BC** |
| $T_3$, ng/mL | 1.4 | 1.4 | 1.2 | 1.2 | 0.1 | BC*** |
| $T_4$, ng/mL | 41.3 | 37.6 | 43.6 | 44.2 | 2.0 | BC* |
| NEFA, mEq/L | 237 | 239 | 248 | 200 | 28 | — |
| LDH (f), IU/mg | 7.6 | 8.1 | 8.0 | 7.7 | 0.4 | — |
| LDH (r), IU/mg | 2.2 | 2.2 | 2.3 | 2.3 | 0.2 | — |
| Julian Calving Date | 76 | 88 | 78 | 114 | 8.5 | G** |
| Calving Rate[5], % | 81 (39/48) | 29 (2/7) | 76 (28/37) | 9 (1/11) | | p < 0.001 |

[1]Deletion of Cytosine is designated as C-
[2]Heat Shock Protein = Hsp70; Growth Hormone = GH; Insulin-like Growth Factor = IGF; Triiodothyronine = $T_3$; Thyroxine = $T_4$; Nonesterified fatty acid = NEFA; Lactate Dehydrogenase = LDH [(f) = forward; (r) = reverse]
[3]G = genotype; BC = body condition; G × BC = interaction
[4]*P < 0.05, P < 0.01, *P < 0.001
[5]Number of observations in parentheses; calving rate was number of bovine subjects that calved divided by total number of bovine subjects in group Single nucleotide polymorphisms found at base positions 1125, 1128, and 895 (deletion) of the bovine Hsp70 gene were most related to calving rates. Bovine subjects with low BC had the lowest calving rate of animals with a SNP at base positions 1125, 1128, and 895 (deletion; 36%, 25% and 9%, respectively). The deletion of the cytosine at base position 895 had the greatest affect on average calving date. Bovine subjects with the deletion had an average calving date of 101 days.

Single nucleotide polymorphisms found at base positions 1125 and 1128 appeared to be related. In 31% of the population, if a SNP occurred at base position 1125, a SNP was present at base position 1128, suggesting a strong association. These SNPs were located in the region in which the putative start of transcription was identified based on the sequence deposited in GenBank. Single nucleotide polymorphisms 1125, 1128, and 1204 were the most frequent SNPs in the population. The deletion of a cytosine at base position 895 was the most dominate and visible in identification from the electropherograms. This deletion occurred 195 base pairs from the beginning of the promoter region.

Bovine subjects with low BC had lower concentrations of $T_3$ than moderate BC bovine subjects while bovine subjects with low BC had higher concentrations of $T_4$ than low BC bovine subjects. Thyroid hormones thyroxine ($T_4$) and tri-iodothronine ($T_3$) are known to affect metabolism and growth.

Plasma concentrations of NEFA were influenced by a genotype×BC interaction; bovine subjects with low BC had higher concentrations of NEFA than moderate BC bovine subjects. Impaired fertility in cattle can be caused by inadequate body condition, and greater BC in beef cattle can result in improved reproductive performance.

Low BC bovine subjects with a SNP at base positions 1125, 1128, and 895 had lower (P<0.05) concentrations of prolactin than bovine subjects without the SNP with the same BC. Prolactin concentrations were influenced by a genotype×BC interaction.

Lactate dehydrogenase activities were affected by a genotype×BC interaction. Low BC bovine subjects with a SNP at base positions 1125 and 1128 had lower (P<0.05) LDH activities than moderate BC bovine subjects with a SNP.

Concentrations of IGF-I were lower in low BC bovine subjects than moderate BC bovine subjects. However, concentrations of GH were not affected by BC. Growth hormone is a regulator of growth and metabolism, and modulates the expression of genes, including IGF-I. When the positive relationship of GH and IGF-I becomes uncoupled, concentrations of GH increase, while reducing IGF-I.

Heat shock protein 70 is induced in response to various stress conditions. However, serum concentrations of Hsp70 were not significantly associated to genotype, body condition or their interaction in this study.

A greater body condition score at calving tends to improve reproductive performance in beef cattle. Nutrient intake and changes in energy reserves of the body can influence reproduction in bovine subjects. Due to these types of changes, bovine subjects with a low body condition score may not become pregnant during the breeding season, or have shorter gestation periods. Results described above indicate bovine subjects with moderate body condition had higher calving rates than bovine subjects with low body condition.

The polymorphisms identified in the promoter region of the bovine heat shock protein 70 gene could be a used as potential genetic markers for selecting Brahman-influenced bovine subjects with a propensity for higher calving rates.

Example 3

Identification of Single Nucleotide Polymorphisms in Coding Region of Bovine LDH-A Gene and their Association with Lactate Dehydrogenase Activity Methods and Materials This study attempted to identify single nucleotide polymorphisms (SNPs) in the coding region of bovine LDH-A that may contribute to risk of fescue toxicosis in the cattle population and correlate this to Angus and Brahman parentages. Bovine subjects of different breeds were used in a long-term genetic and environmental interaction study at the Dale Bumpers Small Farms Research Center in Booneville, Ark. Breeds included Pure Angus (PA, n=42), Pure Brahman (PB, n=42), and reciprocal-cross bovine subjects Angus× Brahman (AB, n=40) and Brahman×Angus (BA, n=37). Blood was collected from each of the 161 animals via jugular venipuncture (Vacutainer, Becton-Dickinson, Rutherford, N.J.). Whole blood was centrifuged at 700×g for 25 min. Serum was decanted and stored in −80° C. until analyzed for LDH activity. Genomic DNA was extracted from white blood cells (buffy coat) using QIAmp blood DNA mini-kit (Qiagen, Valencia, Calif.).

The polynucleotide encoding *Bos taurus* LDH-A (GeneBank accession NM-174099, SEQ ID NO:8) was amplified and sequenced using primers 5'-tccaagatggcaactct-caa-3' (SEQ ID NO:9) and 5'-tgaatccagattgcaaccac-3' (SEQ ID NO:10). The sequences were aligned and analyzed for polymorphisms.

The activity of LDH in the cattle plasma was measured a calorimetric assay using a LDH-L reagent kit (Chiron Diagnostics; East Walpole, Mass.) in a 550 Express Clinical Chemistry Analyzer (Ciba Corning Diagnostics Corp., Alameda, Calif.). LDH activity was determined by measuring the rate of reduction of $NAD^+$ by determining the rate of increase in absorbance at 340 nm. The increase in absorbance at 340 nm is directly proportional to the LDH activity, as LDH catalyzes the oxidation of the lactate to pyruvate with the simultaneous reduction of $NAD^+$ to NADH. The LDH activity was expressed in the international Unit (the amount of enzyme that catalyzes the transformation of 1 μmole of substrate per minute under defined conditions) per liter (U/L).

Allele frequencies were determined for each polymorphism in each population (Table 16). Allele frequencies were compared using contingency table chi-square tests. Preliminary analyses compared allele frequencies between two different forages.

Serum LDH activity data were analyzed as 4×3×2 (breed×3 genotypes for each SNP×forage) factorial arrangement using PROC GLM from SAS (SAS Inst., Cary, N.C.) in an unbalanced design. Means were separately using the PDIFF function of SAS. A value of P≦0.05 was considered statistically significant.

Results

Two new nucleotide polymorphisms were identified, namely g390a and t530c, in the coding region of LDH-A gene. SNP g390a creates a Bsma1 restriction site, and t530c creates a new SSP1 restriction site. However, no interaction among breed, forage and SNP was found.

The SNP g390a is a guanine to adenine substitution in first nucleotide of codon 78 (GTC to ATC) that resulted in the replacement of Valine acid by an Isoleucine. However, SNP t530c (ATT to ATC) resulted in no amino acid change. Three different genotypes (GG, GA, and AA) were observed in SNPg390a. Digestion with BsmA1 yielded two bands (270 and 237 bp) for the GG homozygote (FIG. 1A, GG), three bands (507, 270, and 237 bp) for the GA heterozygote (FIG. 1A, GA), and one band (507 bp) for the AA homozygous variant (FIG. 1A, AA). Digestion with SSP1 produced two bands (375 and 132 bp) in the case of homozygous wild-type (FIG. 1B, TT), three bands (507, 375 and 132 bp) for the TC heterozygote (FIG. 1B, TC) and one band 507 bp for the CC homozygous variant (FIG. 1B, CC).

Genotypic frequencies for these two SNPs showed significant differences among four different breeds of cattle based on a chi-square test (Table 16). All of the PA bovine subjects were GG and TT homozygotes with frequency of 1.0 for both genotypes. This was significantly different from the PB bovine subjects. PB bovine subjects had three different genotypes for both SNPs. About 31.0% or 47.6% of PB cattle were GG and TT homozygous for SNPs g390a and t530c, respectively. GA or TC heterozygous population at both SNPs is 38% in PB bovine subjects. However, 31% of PB bovine subjects were AA variant-homozygous, and only 14.3% for CC variant-homozygotes (Table 16). Interestingly, those AA variant-homozygous bovine subjects at g390a were all TT homozygotes at t530c. CC variant-homozygous bovine subjects at t530c were all GG homozygotes at g390a (data not shown). As for the reciprocal-cross bovine subjects (AB or BA), only two genotypes were observed at each SNP. The GG or TT homozygotes at g390a or t530c were the most frequent in AB bovine subjects with frequency 0.70 or 0.775. In contrast, The GA heterozygotes or TT homozygotes were the most frequent in BA bovine subjects with frequency 0.703 or 0.676 (Table 16). Only 1/37 of BA and 11/42 of PB bovine subjects were GA and TC heterozygous at both SNPs (data not shown).

Results indicated that breed significantly affected allelic frequencies for both g390a and t530c SNPs. Allelic frequencies of the PA bovine subject population were different from those of the PB population at all loci (Table 16). The frequency of the rare allele A ranged from 0 in PA bovine subjects to 0.50 in PB bovine subjects for g390a and allele C from 0 in PA bovine subjects to 0.33 in PB bovine subjects for t530c. The frequency of rare allele A varied in the reciprocal-cross bovine subjects, from 0.15 in AB animals to 0.35 in BA animals, while T allele from 0.11 in AB animals to 0.16 in BA animals (Table 16).

TABLE 16

Distribution of SNPs at the 390 (g390a) or 530 (t530c) nucleotide of LDH-A gene (NM-174099) in different breeds of bovine subjects.

|  | Homozygous or Heterozygous Frequency (number of cattle) | | | Nucleotide Frequency | |
|---|---|---|---|---|---|
| G390A Breed | G/G | G/A | A/A | G | A |
| PA (n = 42) | 1.0 (42) | 0 (0) | 0 (0) | 1.0 | 0 |
| AB (n = 40) | 0.70 (28) | 0.30 (12) | 0 (0) | 0.85 | 0.15 |
| BA (n = 37) | 0.297 (11) | 0.703 (26) | 0 (0) | 0.65 | 0.35 |
| PB (n = 42) | 0.310 (13) | 0.380 (16) | 0.310 (13) | 0.50 | 0.50 |
| T530C Breed | T/T | T/C | C/C | T | C |
| PA (n = 42) | 1.0 (42) | 0 (0) | 0 (0) | 1.0 | 0 |
| AB (n = 40) | 0.775 (31) | 0.225 (9) | 0 (0) | 0.89 | 0.11 |
| BA (n = 37) | 0.676 (25) | 0.324 (12) | 0 (0) | 0.84 | 0.16 |
| PB (n = 42) | 0.476 (20) | 0.381 (16) | 0.143 (6) | 0.67 | 0.33 |

PA = Pure Angus;
AB = Sire is Angus, and Dam is Brahman;
BA = Sire is Brahman, and Dam is Angus;
PB = Pure Brahman There were associations of serum LDH activity with the forage (P<0.05) or breed (P=0.11) (Table 17). The effect of endophyte-infected fescue in cattle depended on breed and SNP. PA bovine subjects grazing Bermuda grass had the lowest LDH activity of 722.5±31.4 U/L, and significantly differed from those grazing Tall fescue grasses; the latter had mean value of 888.5±30.0 U/L (Table 17), that is, the PA bovine subjects grazing Tall Fescue had higher LDH activity than those grazing Bermudagrass (P<0.05). Unlike PA bovine subjects with only one genotype, all PB bovine subjects had three genotypes at both SNPs. In PB bovine subjects with GG genotype at g390a allele, tall fescue significantly increased serum LDH activity (955.8±105.9 U/L), compared with 752.9 (+55.2) U/L in PB individuals grazing Bermuda grass (Table 17). That is, LDH activity of PA bovine subjects grazing Tall fescue grass was higher than LDH activity of PA bovine subjects consuming endophyte-free fescue grass (Table 17). Notably, endophyte-infected fescue had no significant effect on LDH activity in reciprocal cross AB and BA bovine subjects, but had a trend to increase LDH activity in TT homozygous BA bovine subjects (P=0.13) or GA heterozygous BA bovine subjects (P=0.1).

Breed also affected serum LDH activity. In TT homozygous bovine subjects at t530c loci, PA bovine subjects had the lower serum LDH activity (722.5±31.4 U/L) than did those with Brahman sire: 813.6±19.0 U/L for BA 865.5±20.2 U/L for PB (P<0.05, Table 17).

TABLE 17

Means and standard deviations of LDH activity in different breeds of cattle with SNPs at g390a or t530c

| SNP | Genotype | Breed | N | Forage | LDH activity (U/L) |
|---|---|---|---|---|---|
| G390A | GG | PA | 17 | Bermudagrass | 722.5 ± 31.4$^a$ |
|  |  |  | 20 | Tall fescue | 888.5 ± 30.0$^b$ |
|  |  | AB | 16 | Bermudagrass | 790.5 ± 35.1 |
|  |  |  | 12 | Tall fescue | 839.5 ± 35.5 |
|  |  | BA | 5 | Bermudagrass | 740.4 ± 53.9 |
|  |  |  | 4 | Tall fescue | 817.0 ± 29.7 |
|  |  | PB | 7 | Bermudagrass | 752.9 ± 55.2$^c$ |
|  |  |  | 5 | Tall fescue | 955.8 ± 105.9$^d$ |
|  | GA | AB | 6 | Bermudagrass | 807.5 ± 41.3 |
|  |  |  | 6 | Tall fescue | 858.7 ± 56.0 |
|  |  | BA | 17 | Bermudagrass | 815.0 ± 17.9 |
|  |  |  | 8 | Tall fescue | 901.4 ± 22.2 |
|  |  | PB | 12 | Bermudagrass | 818.0 ± 27.8 |
|  |  |  | 4 | Tall fescue | 827.8 ± 50.0 |
|  | AA | PB | 6 | Bermudagrass | 859.0 ± 30.9 |
|  |  |  | 6 | Tall fescue | 874.5 ± 55.5 |
| T530C | TT | PA | 17 | Bermudagrass | 722.5 ± 31.4$^e$ |
|  |  |  | 20 | Tall fescue | 888.5 ± 30.1$^f$ |
|  |  | AB | 15 | Bermudagrass | 787.3 ± 36.8 |
|  |  |  | 16 | Tall fescue | 792.1 ± 53.1 |
|  |  | BA | 16 | Bermudagrass | 813.6 ± 19.0$^f$ |
|  |  |  | 8 | Tall fescue | 901.4 ± 22.2 |
|  |  | PB | 11 | Bermudagrass | 865.5 ± 20.2$^f$ |
|  |  |  | 8 | Tall fescue | 942.1 ± 72.1 |
|  | TC | AB | 7 | Bermudagrass | 812.0 ± 38.2 |
|  |  |  | 2 | Tall fescue | 816.0 ± 154.0 |
|  |  | BA | 6 | Bermudagrass | 756.2 ± 47.3 |
|  |  |  | 4 | Tall fescue | 817.0 ± 29.7 |
|  |  | PB | 11 | Bermudagrass | 775.2 ± 39.3 |
|  |  |  | 4 | Tall fescue | 802.8 ± 24.6 |
|  | CC | PB | 4 | Bermudagrass | 731.0 ± 52.4 |
|  |  |  | 2 | Tall fescue | 829.7 ± 51.8 |

1: $^{a,b}$Within a column, means without a common superscript letter differ significantly at P ≦ 0.05.
2: $^{c,d}$Within a column, means without a common superscript letter differ significantly at P ≦ 0.05.
3. $^{e,f}$Within a column, means without a common superscript letter differ significantly at P ≦ 0.05.
4. N, number animals investigated.

The effect of genotype at t530c on LDH activity was examined, although a significant main model effect of t530c genotype on LDH activity was not detected. Specifically, the LDH activity of PB animals with TT genotypes tended to be higher than those of animals with genotypes TC (P=0.065) or CC (P=0.072). The relationship between LDH-A polymorphisms (g390a and t530c) and milk composition, reproduction, and calf traits are shown in Tables 18 and 19. The g390a SNP was associated with a decreased calving rate (bovine subjects with AA yielded less calves than bovine subjects with GG), an increased milk production (bovine subjects with AA yielded more milk than bovine subjects with GG), and increased calf weaning weight and height (bovine subjects with AA yielded calves with a greater weaning weight and height than bovine subjects with GG). The g390a SNP interacted with body condition to affect serum prolactin concentrations. Specifically, heterozygous cows consuming tall fescue had larger concentrations of prolactin when compared with homozygous cows consuming tall fescue. In contrast homozygous adenine cows consuming bermudagrass had the largest concentration of prolactin compared to all cows. Calf birth weight also was affected by an interaction between genotype and forage. Specifically, homozygous guanine cows consuming tall fescue had the heaviest calves at birth, and homozygous adenine cows grazing bermudagrass had the lightest calves at birth. At the t530c SNP, cows that were homozygous cystosine had lower lifetime calving rates, and heterozygous cows had calves that were heavier and taller at weaning.

TABLE 18

Relationship between LDH-A polymorphisms (g390a) and milk composition, reproduction, and calf traits.

| | Forage | | | | | | | |
| --- | --- | --- | --- | --- | --- | --- | --- | --- |
| | Bermudagrass | | | Fescue | | | | |
| | Genotype | | | | | | | |
| Item | AA | GA | GG | AA | GA | GG | SEM | Effects |
| Calvings, % | 74 | 83 | 86 | 61 | 84 | 83 | 5.8 | g |
| Prolactin, ng/ml | 185 | 88 | 78 | 16 | 34 | 18 | 20.7 | F, g, f * g |
| Milk | | | | | | | | |
| Volume, kg | 12.4 | 13.4 | 12.2 | 10.2 | 10.0 | 8.43 | 1.0 | F, g |
| Butterfat, % | 4.5 | 3.9 | 4.0 | 3.6 | 3.4 | 3.1 | 0.35 | F |
| Protein, % | 3.4 | 3.3 | 3.3 | 3.4 | 3.5 | 3.4 | 0.09 | — |
| SCC, n | 442 | 294 | 312 | 99 | 154 | 260 | 154 | — |
| Calves | | | | | | | | |
| Birth wt, kg | 32.6 | 35.5 | 35.1 | 33.4 | 34.8 | 36.4 | 1.06 | g, g * s |
| Weaning wt, kg | 261 | 266 | 250 | 242 | 242 | 222 | 7.8 | F, G, A |
| Weaning ht, cm | 119 | 118 | 116 | 119 | 117 | 113 | 1.2 | G, S, A |

Effects: for the statistical model main effects were forage (F, f), genotype (G, g), age at weaning (A, a), sex of the calf (S, s), and month (M, m) in the case of multiple dates of collection. Uppercase letters indicate that the main effect was significant at a probability of less than 0.05; whereas, lowercase letters indicates a significance below 0.1. Interactions between main effects are indicated with an asterisk using the same uppercase and lowercase designations.

TABLE 19

Relationship between LDH-A polymorphisms (t530c) and milk composition, reproduction, and calf traits.

| | Forage | | | | | | | |
| --- | --- | --- | --- | --- | --- | --- | --- | --- |
| | Bermudagrass | | | Fescue | | | | |
| | Genotype | | | | | | | |
| | CC | TC | TT | CC | TC | TT | SEM | Effects |
| Calvings, % | 60 | 82 | 87 | 60 | 94 | 79 | 7.7 | G |
| Prolactin, ng/ml | 65 | 125 | 78 | 46 | 30 | 20 | 27.3 | F, g |
| Milk | | | | | | | | |
| Volume, kg | 9.4 | 12.5 | 12.9 | 8.9 | 9.6 | 8.9 | 1.3 | F |
| Butterfat, % | 3.5 | 4.1 | 3.8 | 5.0 | 3.0 | 3.2 | 0.35 | F * G |
| Protein, % | 3.4 | 3.3 | 3.2 | 3.6 | 3.5 | 3.4 | 0.11 | f |
| SCC, n | 206 | 346 | 315 | 89 | 63 | 258 | 157 | — |
| Calves | | | | | | | | |
| Birth wt, kg | 34.3 | 33.7 | 35.6 | 36.8 | 36.2 | 35.5 | 1.35 | f * s |
| Weaning wt, kg | 245 | 262 | 255 | 227 | 247 | 225 | 10.5 | F, G, A |
| Weaning ht, cm | 118 | 118 | 116 | 116 | 117 | 114 | 1.6 | G, S, A |

Effects: for the statistical model main effects were forage (F, f), genotype (G, g), age at weaning (A, a), sex of the calf (S, s), and month (M, m) in the case of multiple dates of collection. Uppercase letters indicate that the main effect was significant at a probability of less than 0.05; whereas, lowercase letters indicates a significance below 0.1. Interactions between main effects are indicated with an asterisk using the same uppercase and lowercase designations.

Example 4

Relationship Between Polymorphisms of the LDH-B Gene and Milk Characteristics in Beef Bovine Subjects Materials and Methods The objective of this study was to determine the genetic diversity in a segment of the LDH-B gene of cattle and its relationship to milk quality and quantity. The bovine subjects used in this study were purebred Angus (n=37), purebred Brahman (n=29), and reciprocal crosses (n=68) from Booneville, Ark. They had grazed on either common bermudagrass or endophyte-infected tall fescue year-round for seven years. Each year, milk was collected during the months of May, June, July, August, and September. The milk was collected using a portable milking machine after a 14 hour separation from their calves (Brown et al., 1996). The quantity of milk was measured in kilograms. Triplicate samples were made to evaluate butterfat content, protein content, and somatic cell count. This was done by a commercial laboratory using a Milkoscan System 4000 (Brown et al., 1996).

Blood samples were collected from each bovine subject via jugular venapuncture and genomic DNA was extracted from the buffy coat. A 452 base pair segment of the polynucleotide encoding Bos taurus LDH-B (SEQ ID NO: 11, GenBank ascession number AJ401268) was PCR amplified and sequenced using primers LDHBF (GTACAGTCCTGCCTG-CATCA, SEQ ID NO:12) and LDHBR (CCATTGTTGA-CACTGGGTGA, SEQ ID NO: 13). Restriction fragment length polymorphisms (RFLP) reaction were determined by digesting the DNA using restriction enzymes PspGI and NcoI (BioLabs, Inc., New England, USA).

The effects of LDH-B genotype and forage type on milk quantity and quality were determined using the PROC MIXED program of SAS. The model included fixed effects of forage, genotype, and forage×genotype interaction. Year and lactation also were included as fixed effects. Days within month was included as a covariate. Random effects were bovine subject*forage*genotype to be used as an error term for forage, genotype and the forage×genotype interaction and bovine subject*lactation*year to be used as an error term for lactation and year. Month was a repeated effect with subject being bovine subject*year.

Results

Five single nucleotide polymorphisms (SNPs) were identified. The SNPs were located at base positions 541, 606, 618, 652, and 669. Restriction enzymes had cut sites located at base positions 606 and 669, PspGI and NcoI, respectively. The LDH-B genotypes at site 606 (A) and site 669 (B). Table 20 shows the distribution of genotypes across breeds. Breed composition was associated (P<0.001) with genotype distribution. Table 20 shows the distribution of genotypes across breeds. The majority of purebred Angus bovine subjects were homozygous adenine at site 606 and homozygous cytosine at site 669. Most of the purebred Brahman cattle were homozygous guanine at site 606 and homozygous thymine at site 669. The cross-bred cattle were primarily heterozygous at both sites. Table 21 shows that the cattle were fairly evenly distributed among genotypes between forage types.

TABLE 20

Frequency of genotypes by breed

| | 606 | | | 669 | | |
|---|---|---|---|---|---|---|
| | GG | GA | AA | CC | CT | TT |
| Angus | 3 | 1 | 35 | 37 | 1 | 1 |
| Crossbred | 2 | 50 | 10 | 8 | 46 | 10 |
| Brahman | 25 | 3 | 2 | 2 | 5 | 22 |
| Total | 30 | 54 | 47 | 47 | 52 | 33 |
| % | 23 | 41 | 36 | 36 | 39 | 25 |

Base sites were 606 and 669. Possible genotypes for each site were GG, GA, and AA for 606 and CC, CT, and TT for 669. Breeds were Angus, Brahman, and reciprocal crosses.

TABLE 21

Frequency of genotype by forage type

| | 606 | | | 669 | | |
|---|---|---|---|---|---|---|
| | GG | GA | AA | CC | CT | TT |
| Bermuda | 17 | 35 | 22 | 23 | 31 | 21 |
| Fescue | 13 | 19 | 25 | 24 | 21 | 12 |

For base sites and genotypes, see Table 20. Forage types were Bermuda or Fescue.

For site 606, milk volume was affected (P<0.05) by the genotype and the month that milk was collected (FIG. 1). Milk volume decreased (P<0.05) for each consecutive month. Bovine subjects that were heterozygous (GA) at 606 produced the largest (P<0.05) amount of milk each month. Bovine subjects that were homozygous adenine produced a similar (P<0.01) amount of milk as homozygous guanine bovine subjects initially but had the lowest (P<0.05) milk production during the last three months of collection. Homozygous cytosine bovine subjects had lower milk production than the heterozygous bovine subjects, and the homozygous thymine bovine subjects had intermediate milk production (8.2, 10.4, and 9.2 kg/d SE=1.3, respectively).

Figure 2:
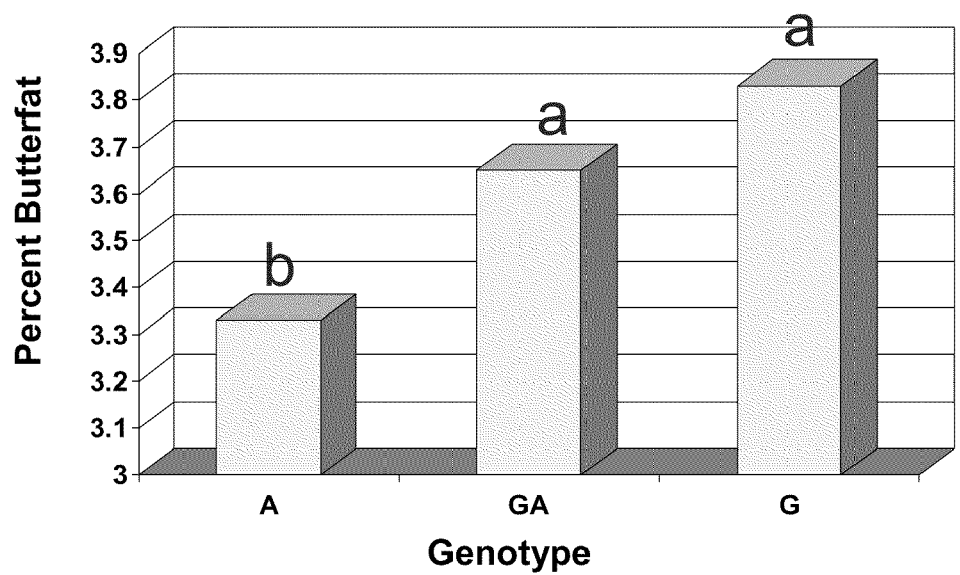
FIG. 2 is a graph showing the effect of different genotypes at position 606 of the polynucleotide encoding bovine LDH-B on the percent butterfat in milk produced by bovine subjects.

FIG. 2 demonstrates that butterfat percent was affected (P<0.01) by genotype at site 606. The homozygous guanine bovine subjects, did not show a statistical difference from the heterozygous (GA) bovine subjects, and produced milk with the highest percent butterfat. Bovine subjects that were homozygous adenine produced milk with the lowest (P<0.01) butterfat content.

Figure 3:
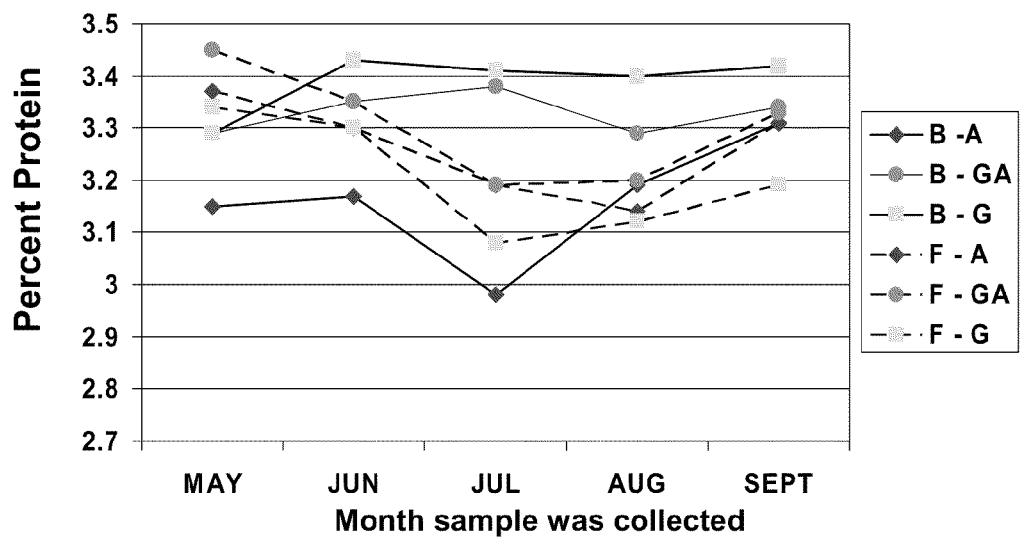
FIG. 3 is a graph showing interaction effects of forage type, collection month, and different genotypes at position 606 of the polynucleotide encoding bovine LDH-B on the percent protein in milk produced by bovine subjects.
Figure 4:
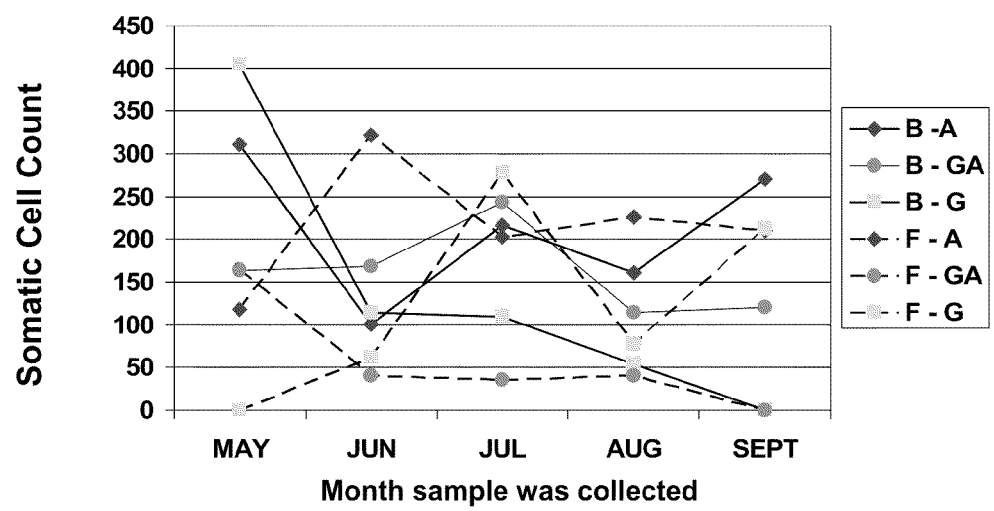
FIG. 4 is a graph showing interaction effects of forage type, collection month, and different genotypes at position 606 of the polynucleotide encoding bovine LDH-B on the somatic cell count (SCC) of bovine subjects.

As shown in FIG. 3, there was a three-way interaction affecting (P<0.01) protein content including genotype at site 606, month the milk was collected, and forage grazed. The bovine subjects that were homozygous adenine and on bermudagrass had lower protein content for the first three months. All the bovine subjects on fescue had similar protein levels, showing a decrease for the first three months then an increase for the last two. The heterozygous (GA) bovine subjects and homozygous guanine bovine subjects were fairly constant. FIG. 4 indicates that SCC was affected (P<0.05) by genotype at site 606, month the milk was collected, and forage grazed, but there appears to be no discernible pattern.

Figure 5:
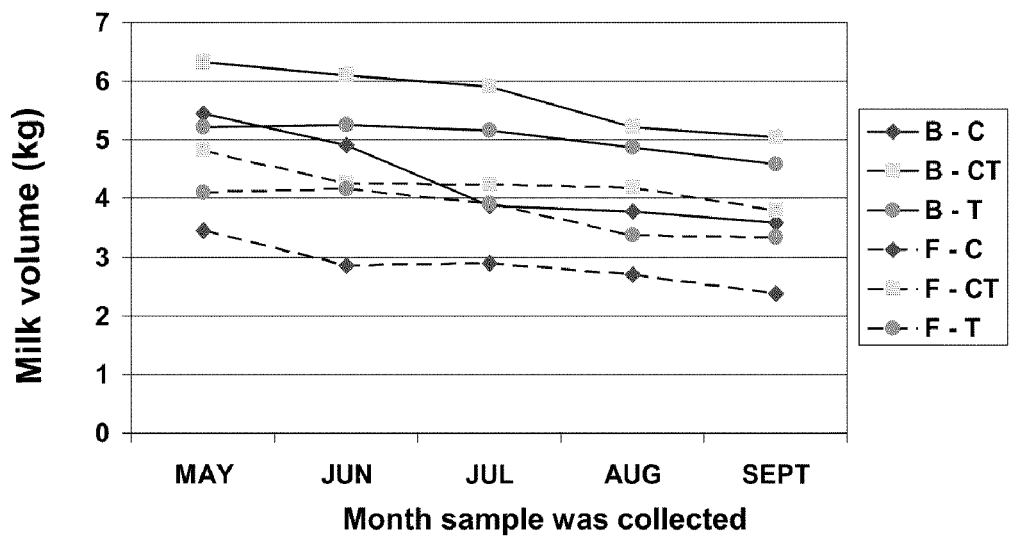
FIG. 5 is a graph showing interaction effects of forage type, collection month, and different genotypes at position 669 of the polynucleotide encoding bovine LDH-B on the milk volume produced by bovine subjects.

FIG. 5, illustrates how milk volume was affected (P<0.01) by genotype at site 669, month of milk collection, and forage type. In general, the bovine subjects that grazed common Bermudagrass produced more milk than those that grazed endophyte-infested tall fescue. Within each forage group, the bovine subjects that were heterozygous (CT) produced more milk than both homozygous genotypes. Overall, milk volume decreased with each consecutive month.

Figure 6:
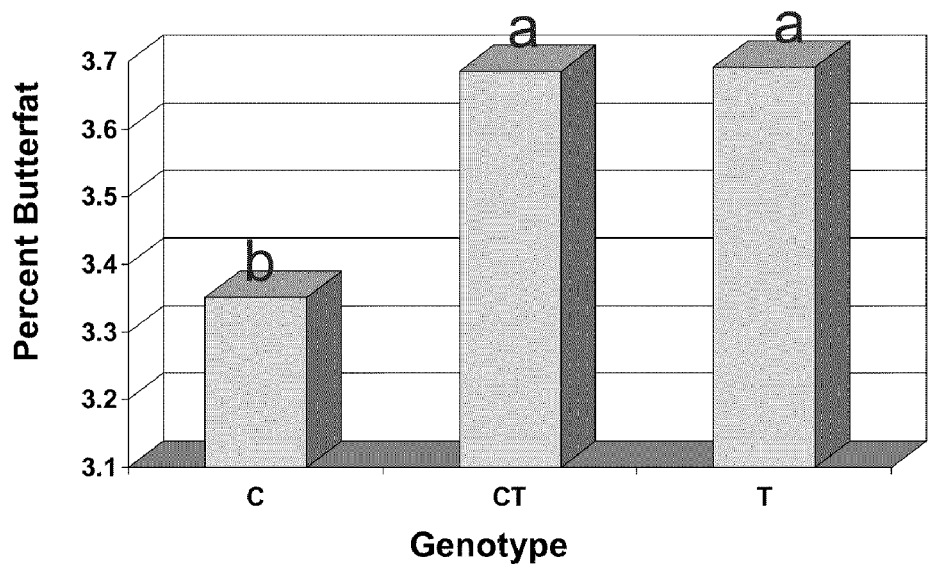
FIG. 6 is a graph showing the effect of different genotypes at position 669 of the polynucleotide encoding bovine LDH-B on the percent butterfat in milk produced by bovine subjects.

The genotype at site 669 was the only factor that affected (P<0.05) butterfat percent, FIG. 6. Those bovine subjects that were heterozygous and homozygous thymine produced milk with more (P<0.05) butterfat than the homozygous cytosine bovine subjects.

Figure 7:
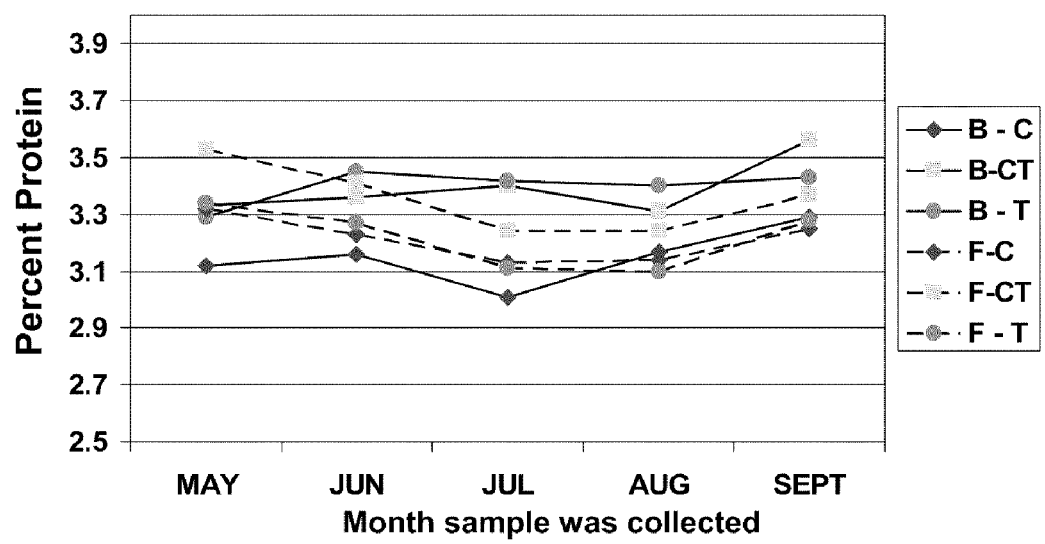
FIG. 7 is a graph showing interaction effects of forage type, collection month, and different genotypes at position 669 of the polynucleotide encoding bovine LDH-B on percent protein in milk produced by bovine subjects.

FIG. 7 shows that percent protein in the milk was affected (P<0.05) by a three-way interaction involving genotype at site 669, month milk was collected, and forage type. Homozygous cytosine bovine subjects produced the least amount of protein the first three months, and those that were on bermudagrass produced less than those on fescue. The last two months, the homozygous cytosine individuals produced about the same amount of protein as the homozygous thymine individuals on fescue. The homozygous thymine bovine subjects that were on bermudagrass, produced the most protein during months 2, 3, and 4; they stayed consistent for all months except the first.

Figure 8:
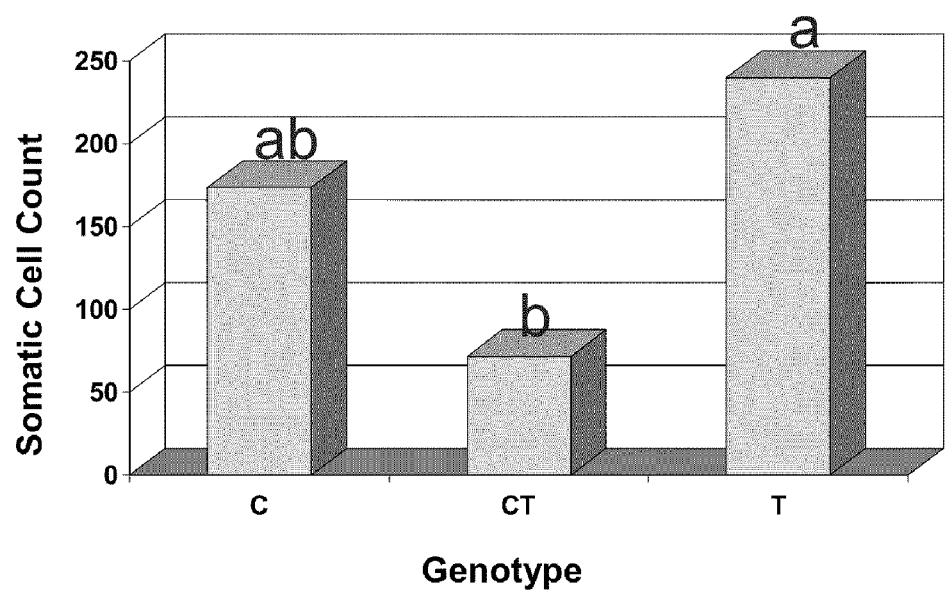
FIG. 8 is a graph showing the effect of different genotypes at position 669 of the polynucleotide encoding bovine LDH-B on the somatic cell count (SCC) in milk from bovine subjects.

As shown in FIG. 8, somatic cell count was affected (P<0.05) by genotype at site 669. Bovine subjects that were heterozygous (CT) had the lowest SCC; their milk was not statistically different from the homozygous cytosine bovine subjects, but it was different (P<0.05) from the homozygous thymine bovine subjects, which had the highest SCC.

The relationship between LDH-B polymorphisms (a618g and c669t) and milk composition, reproduction, and calf traits are shown in Tables 22 and 23. The a618g SNP was associated with a decreased calving rate (bovine subjects with AA and AG had a greater calving rate than bovine subjects with GG), a greater volume of milk produced (bovine subjects with AG and GG yielded more milk than bovine subjects with AA), more butterfat in the milk produced (bovine subjects with AG and GG yielded milk with more butterfat than bovine subjects with AA), and a greater calf weaning height (bovine subjects with AG and GG yielded calves with a greater weaning height than bovine subjects with AA). The a618g SNP also affected calf birth weight and weaning weight. The c669t SNP was associated with increased milk production (bovine subjects with TT yielded more milk than bovine subjects with CC), and increased calf weaning weight and height (bovine subjects with TT yielded calves with a greater weaning weight and height than bovine subjects with CC). The c669t SNP also affected the calving rate and calf birth weight. Homozygous cytosine cows consuming tall fescue had the lowest lifetime calving percent. Furthermore, calves from homozygous cytosine cows had calves with the lowest body weight and shortest hip height at weaning.

TABLE 22

Relationship between LDH-B polymorphisms (a618g) and milk composition, reproduction, and calf traits.

| | Forage | | | | | | | |
|---|---|---|---|---|---|---|---|---|
| | Bermudagrass | | | Tall Fescue | | | | |
| | Genotype | | | | | | | |
| Item | AA | AG | GG | AA | AG | GG | SEM | Effects |
| Calvings, % | 87 | 87 | 63 | 66 | 97 | 75 | 7.6 | G, f * g |
| Prolactin, ng/ml | 80 | 84 | 122 | 20 | 17 | 33 | 29.3 | F |
| Milk | | | | | | | | |
| Volume, kg | 11.9 | 13.9 | 11.6 | 6.6 | 9.5 | 9.7 | 1.4 | F, g |
| Butterfat, % | 3.0 | 3.6 | 4.1 | 2.5 | 2.8 | 3.4 | 0.4 | F, G |
| Protein, % | 3.1 | 3.3 | 3.2 | 3.3 | 3.3 | 3.4 | 0.11 | f |
| SCC, n | 168 | 258 | 243 | 341 | 430 | 76 | 218 | — |
| Calves | | | | | | | | |
| Birth wt, kg | 35.5 | 33.3 | 34.8 | 34.8 | 36.0 | 33.7 | 1.57 | s, G * S |
| Weaning wt, kg | 246 | 266 | 259 | 191 | 249 | 234 | 10.5 | F, G, F * G, S, A |
| Weaning ht, cm | 113 | 117 | 117 | 108 | 117 | 117 | 1.6 | f, G, f * g, S, A |

Effects: for the statistical model main effects were forage (F, f), genotype (G, g), age at weaning (A, a), sex of the calf (S, s), and month (M, m) in the case of multiple dates of collection. Uppercase letters indicate that the main effect was significant at a probability of less than 0.05; whereas, lowercase letters indicates a significance below 0.1. Interactions between main effects are indicated with an asterisk using the same uppercase and lowercase designations.

TABLE 23

Relationship between LDH-B polymorphisms (c669t) and milk composition, reproduction, and calf traits.

| | Forage | | | | | | | |
|---|---|---|---|---|---|---|---|---|
| | Bermudagrass | | | Forage | | | | |
| | Genotype | | | | | | | |
| Item | CC | TC | TT | CC | TC | TT | SEM | Effects |
| Calvings, % | 87 | 83 | 75 | 66 | 96 | 80 | 7.3 | f * g |
| Prolactin, ng/ml | 80 | 94 | 117 | 21 | 13 | 26 | 29.2 | F |

TABLE 23-continued

Relationship between LDH-B polymorphisms (c669t) and milk composition, reproduction, and calf traits.

|  | Forage | | | | | | | |
|---|---|---|---|---|---|---|---|---|
|  | Bermudagrass Genotype | | | Forage Genotype | | | | |
| Item | CC | TC | TT | CC | TC | TT | SEM | Effects |
| Milk |  |  |  |  |  |  |  |  |
| Volume, kg | 11.6 | 13.3 | 12.0 | 6.5 | 9.6 | 8.2 | 1.3 | F, g |
| Butterfat, % | 2.9 | 3.4 | 3.9 | 2.5 | 2.9 | 2.9 | 0.38 | F |
| Protein, % | 3.2 | 3.3 | 3.2 | 3.4 | 3.4 | 3.4 | 0.1 | F |
| SCC, n | 123 | 246 | 169 | 352 | 87 | 376 | 199 | — |
| Calves |  |  |  |  |  |  |  |  |
| Birth wt, kg | 36.1 | 34.8 | 33.9 | 35.1 | 37.2 | 35.2 | 1.45 | S, g * s |
| Weaning wt, kg | 255 | 264 | 260 | 190 | 244 | 240 | 9.5 | F, G, f * g, S, A |
| Weaning ht, cm | 114 | 118 | 117 | 109 | 117 | 116 | 1.5 | F, G, S, A |

Effects: for the statistical model main effects were forage (F, f), genotype (G, g), age at weaning (A, a), sex of the calf (S, s), and month (M, m) in the case of multiple dates of collection. Uppercase letters indicate that the main effect was significant at a probability of less than 0.05; whereas, lowercase letters indicates a significance below 0.1. Interactions between main effects are indicated with an asterisk using the same uppercase and lowercase designations.

Example 5

Sequencing and Identifying Polymorphisms in the Enhancer Region of the Bovine Prolactin Gene Materials and Methods Polymorphisms in the enhancer region of the PRL gene were located and correlated to Brahman and Angus parentages. Genomic DNA was obtained from 17 Brahman (BB), 12 Brahman/Angus (BA), 21 Angus/Brahman (AB), and 23 Angus (AA) bovine subjects. Primers+PRL 892 (AAGTC-CCCATAAGCACACTTGG) (SEQ ID NO: 15) and −PRL 1392 (CTAACTTTAGGGAGTTCATACTG) (SEQ ID NO: 16) were used to PCR amplify and sequence a 500 base pair fragment from positions −892 to −1392 of the 5' flanking polynucleotide regulatory region of the Bos Taurus prolactin gene (GenBank accession number X16641, SEQ ID NO: 14).

The restriction enzymes Xba I (TCT AGA, Promega) and Hsp92II (CATG, Promega) were used to digest the PCR products from all 73 samples, and the products were separated and analyzed using gel electrophoresis.

Results

Two SNPs were identified at positions −1286 (a cytosine to a thymine) and −1161 (an adenine to a guanine).

Two of the SNPs identified in the initial sequencing were tested on 93 additional samples to assess the frequency of the polymorphisms. Of the 93 test samples 73 were successfully amplified and restriction digested with Hsp92II and Xba I. If the allele had the SNP at −1286 (TTTAGA), the Xba I did not digest at this designated site, but the original sequence would be digested (TCTAGA). If the allele had the SNP at −1161 (CGTG), the Hsp92II did not digest at this position; yet if the allele was CATG, the enzyme did digest. The alleles that did not contain the SNP were coded as 'W' for Xba I and 'Y' for Hsp92II, also referred to as 'cuts'. Those alleles that had the SNPs were labeled as 'X' for Xba I and 'Z' for Hsp92II, known as 'uncuts'.

Xba I. For the −1286 SNP, samples were homozygously cut (alleles WW), heterozygous (both alleles WX), or completely uncut (alleles XX). The samples that were homozygous for the SNP, showed a band at 500 only, while those that were heterozygous showed bands at 106, 394, and 500. The Xba I enzyme digested those alleles without the SNP to create a 106 bp and a 394 bp fragment. The allelic distributions are presented in Table 25. By examining this data, a significant dependence between breed composition and the allelic frequencies was found. Both maternal and paternal breed were important (P<0.05 maternal, P<0.01 paternal). The frequencies of alleles show a near perfect distribution between W and X.

TABLE 24

Allele frequencies of Hsp92II restriction site by breed composition.

| Breed[1] | YY[2] | YZ | ZZ |
|---|---|---|---|
| AA | 23 | 0 | 0 |
| AB | 17 | 4 | 0 |
| BA | 5 | 7 | 0 |
| BB | 8 | 9 | 0 |

[1]Breed designations are AA = purebred Angus; AB = sire is Angus, dam is Brahman; BA = sire is Brahman, dam is Angus; BB = purebred Brahman.
[2]Allele YY represents the samples that were homozygous for the restriction site allele (CATG), YZ represents the heterozygous bovine subjects, and ZZ allele represents the samples that were homozygous for the SNP (CGTG).

TABLE 25

Allele frequencies of Xba I restriction site by breed composition.

| Breed[1] | WW[2] | WX | XX |
|---|---|---|---|
| AA | 8 | 13 | 2 |
| AB | 1 | 19 | 1 |
| BA | 3 | 6 | 3 |
| BB | 1 | 8 | 8 |

[1]Breed designations are AA = purebred Angus; AB = sire is Angus, dam is Brahman; BA = sire is Brahman, dam is Angus; BB = purebred Brahman.
[2]Allele WW represents the samples that were homozygous for the restriction site allele (TCTAGA), YZ represents the heterozygous bovine subjects, and ZZ allele represents the samples that were homozygous for the SNP (TTTAGA).

Hsp92II. For the −1161 SNP, samples were homozygously cut (alleles YY), or heterozygous for the cut (both alleles YZ), but no samples were completely uncut (alleles ZZ). Heterozygosity was determined by the appearance of bands for both cut and uncut fragments. Due to other Hsp92II digestion sites in the region, the 500 bp sequence will have a 167 bp fragment, a 220 bp fragment, and a 113 bp if the SNP at −1161 was present in both alleles (YY). If only one allele has the polymorphism (YZ), bands are visible at 220, 167, 113, 118, and 102, while a bovine subject that was homozygous for the polymorphism would have bands at 167, 118, 113, and 102 only; however, no samples showed this pattern. Table 24 presents the allelic frequency of animals by breed composition, showing that the breed did affect the distribution of Hsp92II alleles (P<0.001). Additional analysis showed that paternal breed had a significant affect on the distribution of alleles with Brahman sires carrying 80% of the YZ combination of alleles. The maternal breed was not a significant source of variation of frequencies of this Hsp92II allele. The sequences that contained the Z allele were either crossbred or Brahman DNA samples; this distribution contributes to the low allele frequency of 0.137 for this population.

Allelic Interaction By examining the polymorphism frequencies together it is revealed that both alleles are significantly affected by the breed composition. These interactions, shown in Table 26, demonstrate that several possible allele combinations are not present in the population. As there are no homozygous Z samples, there are no ZZ samples that are paired with either Xba I allele. Another omission is that the heterozygous Hsp92II alleles (YZ) did not combine with the homozygous alleles for uncut in Xba I.

TABLE 26

Allelic Combinations based on breed composition.

| Breed[2] | Xba I | | | | | | | | |
|---|---|---|---|---|---|---|---|---|---|
| | WW[1] | | | WX Hsp92II | | | XX | | |
| | YY | YZ | ZZ | YY | YZ | ZZ | YY | YZ | ZZ |
| AA | 8 | 0 | 0 | 13 | 0 | 0 | 2 | 0 | 0 |
| AB | 0 | 1 | 0 | 16 | 3 | 0 | 1 | 0 | 0 |
| BA | 0 | 3 | 0 | 2 | 4 | 0 | 3 | 0 | 0 |
| BB | 0 | 1 | 0 | 0 | 8 | 0 | 8 | 0 | 0 |

[1]Allele WW represents the samples that were homozygous for the restriction site allele (TCTAGA), YZ represents the heterozygous bovine subjects, and ZZ allele represents the samples that were homozygous for the SNP (TTTAGA). Allele YY represents the samples that were homozygous for the restriction site allele (CATG), YZ represents the heterozygous bovine subjects, and ZZ allele represents the samples that were homozygous for the SNP (CGTG).
[2]Breed designations are AA = purebred Angus; AB = sire is Angus, dam is Brahman; BA = sire is Brahman, dam is Angus; BB = purebred Brahman.

Both SNPs showed allelic frequency variation between the Brahman and Angus populations. On the polymorphism at −1286, Brahmans were the predominant carriers with fewer carriers in the Angus population. This SNP has an allele frequency of 0.507. The polymorphism at −1161 showed even more variation in that the Brahmans appear to be the only carriers of the allele, with a frequency of 0.137.

For the Xba I site, there was a significant variation in the frequency of alleles between the purebred Angus and the purebred Brahman. In the AAs, only 8.7% of the samples were homozygous for the uncut allele (XX), while the BBs had only 47% homozygous for the same allele. This indicated that the TTTAGA allele exists in the Angus population, but at a lower frequency than in the Brahman population. At the Hsp92II site, the Brahman-sired bovine subjects were more likely to be heterozygous for the trait than those sired by Angus. This indicated that the CGTG allele (Y) predominantly originates in the Brahman population.

The only bovine subjects to be cut by both Hsp92II and Xba I were purebred Angus, while the Brahman influence provided the alleles for heterozygosity. There were no Xba I uncut samples (XX) that are Hsp92II heterozygous (YZ). Due to the proximity of these SNPs, which are only 125 base pairs apart, it is highly probable that their frequencies are not independent. Together these polymorphisms provided a genetic marker for the Bos taurus and Bos indicus species on the enhancer region of the PRL gene.

Effects of bovine subject genotype, forage, and their interactive effects on bovine subject productivity traits are presented in Tables 27 and 28. The a-1161g (Hsp92II) SNP was associated with increased prolactin (bovine subjects with AG had more prolactin than bovine subjects with AA), increased milk protein (bovine subjects with AG yielded milk with more protein than bovine subjects with AA), decreased SCC (bovine subjects with AG has less SCC than bovine subjects with AA), and increased calf weaning weight and height (bovine subjects with AG yielded calves with a greater weaning weight and height than bovine subjects with AA). Heterozygous cows at the a-1161g (Hsp92II) SNP had lower somatic cell counts in their milk, and heavier and taller calves at weaning. The c-1286t (XbaI) SNP was associated with increased calf weaning height (bovine subjects with TT yielded calves with a greater weaning height than bovine subjects with CC). The c-1286t (XbaI) SNP also affected the calving rate (homozygous thymine cows grazing tall fescue had lower calving rates compared to all other groups of cows) and milk butterfat (homozygous cytosine cows grazing tall fescue had the lowest milk butterfat percent).

TABLE 27

Relationship between prolactin promoter restriction enzyme (Hsp92II) digestion (a-1161g SNP) and milk composition, reproduction, and calf traits.

| | Forage | | | | | |
|---|---|---|---|---|---|---|
| | Bermudagrass | | Tall Fescue | | | |
| | Genotype | | | | | |
| Item | AA | AG | AA | AG | SEM | Effects |
| Calvings, % | 88 | 76 | 78 | 89 | 5.7 | F * G |
| Prolactin, ng/ml | 87 | 171 | 15 | 26 | 24. | F, g |
| Milk | | | | | | |
| Volume, kg | 12.3 | 11.4 | 8.4 | 9.3 | 0.79 | F |
| Butterfat, % | 4.2 | 3.8 | 3.2 | 3.2 | 0.29 | F |
| Protein, % | 3.2 | 3.3 | 3.4 | 3.6 | 0.08 | F, g |
| SCC, n | 364 | 159 | 330 | 134 | 110 | G, |
| Calves | | | | | | |
| Birth wt, kg | 35.6 | 34.4 | 35.1 | 37.1 | 0.93 | f * g |
| Weaning wt, kg | 251 | 257 | 219 | 245 | 7.3 | F, G, S, A |
| Weaning ht, cm | 115 | 118 | 112 | 117 | 1.15 | f, G, S, A |

Effects: for the statistical model main effects were forage (F, f), genotype (G, g), age at weaning (A, a), sex of the calf (S, s), and month (M, m) in the case of multiple dates of collection. Uppercase letters indicate that the main effect was significant at a probability of less than 0.05; whereas, lowercase letters indicates a significance below 0.1. Interactions between main effects are indicated with an asterisk using the same uppercase and lowercase designations.

TABLE 28

Relationship between prolactin promoter restriction enzyme (XbaI) digestion (c-1286t SNP) and milk composition, reproduction, and calf traits.

| | Forage | | | | | | | |
|---|---|---|---|---|---|---|---|---|
| | Bermudagrass | | | Tall Fescue | | | | |
| | Genotype | | | | | | | |
| Item | CC | CT | TT | CC | CT | TT | SEM | Effects |
| Calvings, % | 88 | 83 | 88 | 90 | 84 | 58 | 7 | f * g |
| Prolactin, ng/ml | 91 | | 103 | 13 | 17 | 25 | 33 | F |
| Milk | | | | | | | | |
| Volume, kg | 12.2 | 12.5 | 11.4 | 8.4 | 9.2 | 7.3 | 1.02 | F |
| Butterfat, % | 4.6 | 4.3 | 3.8 | 2.7 | 3.6 | 3.8 | 0.35 | F, F * G |
| Protein, % | 3.1 | 3.2 | 3.3 | 3.5 | 3.4 | 3.6 | 0.1 | F |
| SCC, n | 437 | 277 | 311 | 140 | 346 | 253 | 163 | — |
| Calves | | | | | | | | |
| Birth wt, kg | 35.2 | 35.0 | 35.7 | 37.0 | 35.5 | 34.3 | 1.21 | — |
| Weaning wt, kg | 240 | 256 | 259 | 227 | 230 | 226 | 9.5 | F, S, A |
| Weaning ht, cm | 114 | 117 | 118 | 113 | 114 | 116 | 1.5 | g, S, A |

Effects: for the statistical model main effects were forage (F, f), genotype (G, g), age at weaning (A, a), sex of the calf (S, s), and month (M, m) in the case of multiple dates of collection. Uppercase letters indicate that the main effect was significant at a probability of less than 0.05; whereas, lowercase letters indicates a significance below 0.1. Interactions between main effects are indicated with an asterisk using the same uppercase and lowercase designations.

Example 6

Genomic Comparisons of Bovine CYP3A28 of Angus, Brahman, and Reciprocal Crosses in Correlation to Fescue Toxicosis Materials and Methods The frequency of single nucleotide polymorphism (SNP) 994 in the CYP3A28 sequence (encoding cytochrome P450) of three breed types of cattle was determined, and the distribution of genotype among the breed types was compared to previously collected data concerning productivity traits while on endophyte-infected tall fescue in order to explain the differing responses of the breed types to the toxic ergot alkaloids.

Bovine subjects (n=121) were part of a long-term animal breeding project at the Dale Bumpers Small Farm Research Center near Booneville, Ark. Breed group distribution was as follows: Angus (Bos taurus; n=28), Brahman (Bos indicus; n=33), and Angus Brahman reciprocal crosses (n=60). Bovine subjects were maintained in breeding groups of approximately 20 animals. Breeding groups were assigned to one of two forage types (endophyte-infected tall fescue or bermudagrass), and the bovine subjects remained on that forage year round for the life of the project.

Genomic DNA was prepared from the buffy coat of each bovine subject using spin-tube method (Qiagen, Inc., Valrucia, Calif.). A 565 base sequence within the polynucleotide encoding B. taurus cytochrome P450 (SEQ ID NO: 17, gene CYP3A28, GenBank accession number Y10214) was PCR amplified using specific primers P450f (5'-CAACAACAT-GAATCAGCCAGA-3', SEQ ID NO:18) and P450r (3'-CCTACATTCCTGTGTGTGCAA-5', SEQ ID NO:19). Following amplification, 16 samples were sequenced, and a single nucleotide polymorphism (SNP) was established at base 994.

The amplification product from each sample was digested with Alu I (New England BioLabs) and analyzed on agarose gels. All bovine subjects were genotyped using RFLP analysis, and bovine subjects were classified as either homozygous cytosine (CC) or guanine (GG), or heterozygous (GC) based on their respective gel separation.

Genotype distributions and frequencies were evaluated by Chi-square analysis to determine the effects of breed group, sire breed, and dam breed. Analysis of variance was used to determine the effects of genotype, forage, and the interaction of genotype and forage type on lifetime calving rate, milk quality and quantity, and calf weaning weight and height.

Results

The polymorphism was a transversion consisting of either a cytosine or guanine, and occurred at an Alu I restriction site (AG/CT). From the sequences, three possible genotypes were established, homozygous cytosine (CC) or guanine (GG), or heterozygous (GC). Distribution of CYP3A28 genotypes was affected (P<0.05) by breed group classification (Table 29). Approximately one-half of the bovine subjects (49%) were identified as homozygous cytosine (CC) at the SNP location. Twelve percent of the remaining bovine subjects were homozygous guanine (GG) at base 994. Most (61%) of the Angus bovine subjects were heterozygous (GC) at the SNP location. However, the crossbred and purebred Brahman bovine subjects were predominately homozygous cytosine (CC) at base 994 (52 and 64%, respectively).

TABLE 29

Breed type by genotype interaction (P < 0.05).

| Frequency Row Percent | CC | GC | GG | TOTAL |
|---|---|---|---|---|
| AA | 7 | 17 | 4 | 28 |
| | 25 | 61 | 14 | 23 |
| Crossbreeds | 31 | 23 | 6 | 60 |
| | 52 | 38 | 10 | 50 |
| BB | 21 | 8 | 4 | 33 |
| | 64 | 24 | 12 | 27 |
| Total | 59 | 48 | 14 | 121 |
| | 49 | 40 | 12 | 100 |

*AA = Angus, BB = Brahman, Crossbreeds = AB and BA

Both sire breed (P<0.08) and dam breed (P<0.05) affected CYP3A28 genotype distribution (Tables 30 and 31, respectively). Most (~50%) bovine subjects sired by Angus bulls or that had Angus dams were heterozygous at base 994. However, bovine subjects with Brahman sires or Brahman dams were skewed (56-59%) toward the homozygous cytosine genotype.

TABLE 30

Sire breed type by genotype interaction (P < 0.08).

| Frequency Row Percent | CC | GC | GG | Total |
|---|---|---|---|---|
| AA | 24 | 29 | 6 | 59 |
|  | 41 | 49 | 10 |  |
| BB | 35 | 19 | 8 | 62 |
|  | 56 | 31 | 13 |  |
| Total | 59 | 48 | 14 | 121 |

TABLE 31

Dam breed type by genotype interaction (P < 0.05).

| Frequency Row Percent | CC | GC | GG | Total |
|---|---|---|---|---|
| AA | 21 | 28 | 8 | 57 |
|  | 37 | 49 | 14 |  |

TABLE 31-continued

Dam breed type by genotype interaction (P < 0.05).

| Frequency Row Percent | CC | GC | GG | Total |
|---|---|---|---|---|
| BB | 38 | 20 | 6 | 64 |
|  | 59 | 31 | 9 |  |
| Total | 59 | 48 | 14 | 121 |

Figure 9:
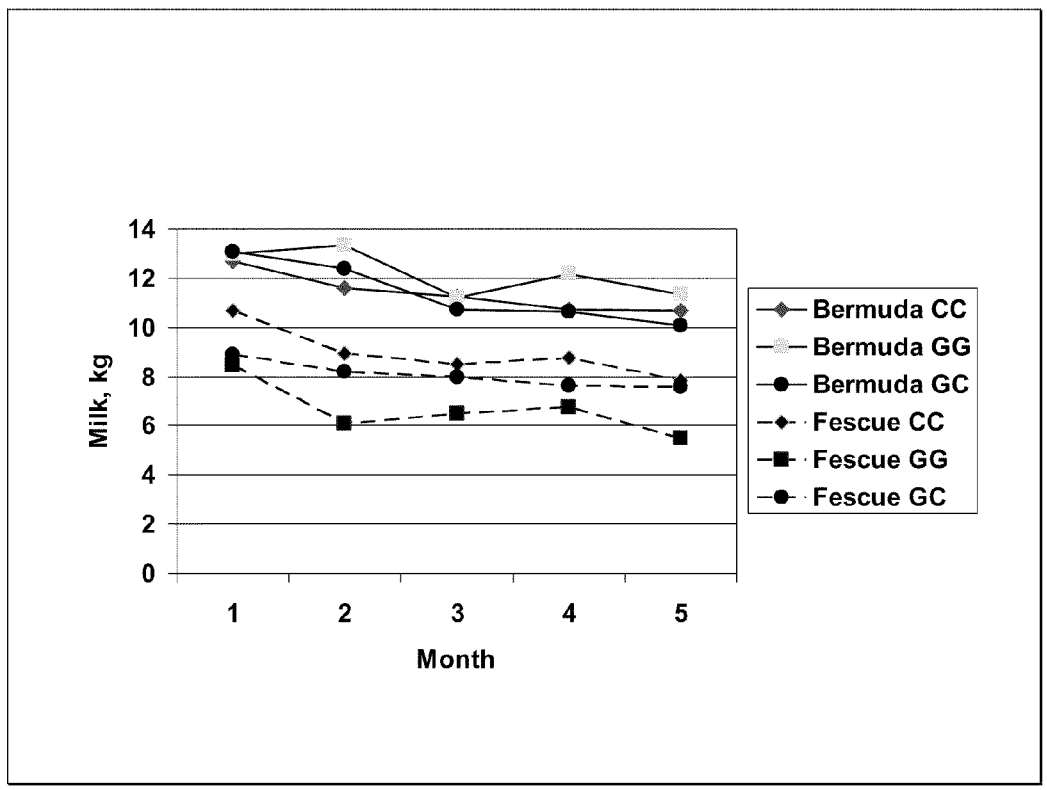
FIG. 9 is a graph showing interaction effects of forage type, collection month, and different genotypes at position 994 of the polynucleotide encoding bovine cytochrome P450 on the amount of milk produced by bovine subjects.
Figure 10:
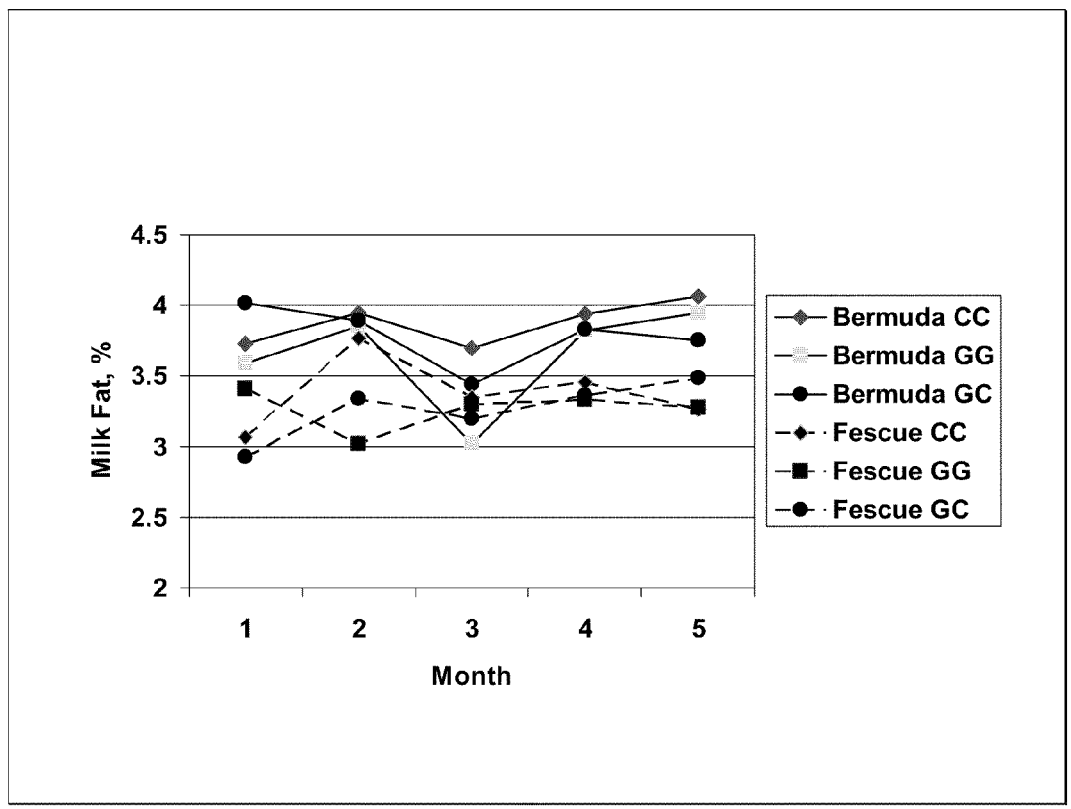
FIG. 10 is a graph showing interaction effects of forage type, collection month, and different genotypes at position 994 of the polynucleotide encoding bovine cytochrome P450 on percent butterfat in milk produced by bovine subjects.
Figure 11:
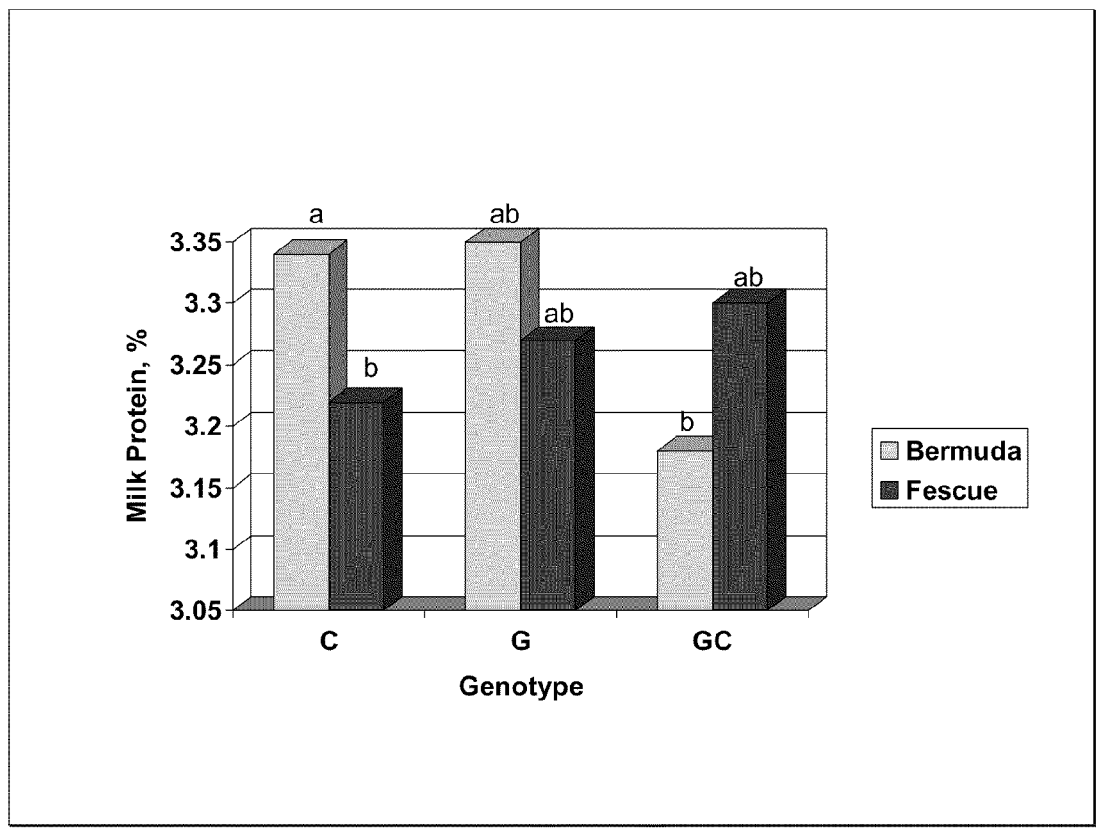
FIG. 11 is a graph showing the effect of forage type and different genotypes at position 994 of the polynucleotide encoding bovine cytochrome P450 on the percent protein in milk produced by the bovine subjects.

Effects of bovine subject genotype, forage, and their interactive effects on bovine subject productivity traits are presented in Table 32. Lifetime calving percentage, calf birth weight, and somatic cell counts in milk were not affected (P>0.2). Serum prolactin concentrations were lower (P<0.01) in bovine subjects that grazed tall fescue forage when compared to those of bovine subjects grazing bermudagrass (20 vs. 95 ng/mL, respectively). Milk volume, butterfat percent, and milk protein percent were affected (P<0.07) by interactions of forage, genotype, and month of sampling. Bovine subjects grazing tall fescue numerically had lower milk production than bovine subjects grazing bermudagrass. Bovine subjects with genotype homozygous guanine (GG) and grazing tall fescue produced the least amount of milk during the sampling period (FIG. 9). Milk fat percentage was not consistently affected by forage type or bovine subject genotype, and those fluctuations resulted in a three-way interaction (P<0.07) between bovine subject genotype, forage type, and month of sampling (FIG. 10). Protein percent in the milk of bovine subjects was affected by an interaction (P<0.07) between forage type and bovine subject genotype (FIG. 11). Heterozygous (GC) bovine subjects grazing bermudagrass and homozygous cytosine (CC) grazing tall fescue had lower (P<0.05) milk protein concentrations than homozygous cytosine bovine subjects grazing bermudagrass.

TABLE 32

Relationship between Alu I-digested cytochrome P450 3A28 (SNP at 994) and milk composition, reproduction, and calf traits.

| | Forage | | | | | | | |
|---|---|---|---|---|---|---|---|---|
| | Bermudagrass | | | Tall Fescue | | | | |
| | Genotype | | | | | | | |
| Item | CC | GC | GG | CC | GC | GG | SEM | Effects |
| Calvings, % | 75 | 86 | 82 | 88 | 81 | 90 | 6.2 | — |
| Prolactin, ng/ml | 74 | 114 | 97 | 25 | 24 | 10 | 21.7 | F |
| Milk | | | | | | | | |
| Volume, kg | 11.4 | 11.4 | 12.2 | 9.0 | 8.1 | 6.7 | 0.97 | F, f * g * m |
| Butterfat, % | 3.88 | 3.79 | 3.64 | 3.38 | 3.26 | 3.27 | 0.21 | F, f * g * m |
| Protein, % | 3.34 | 3.18 | 3.35 | 3.22 | 3.3 | 3.27 | 0.07 | F * G, F * M, G * M |
| SCC, n | 121 | 225 | 147 | 44 | 94 | 65 | 94 | — |
| Calves | | | | | | | | |
| Birth wt, kg | 36 | 35 | 35 | 36 | 36 | 36 | 1.2 | — |
| Weaning wt, kg | 260 | 253 | 264 | 234 | 231 | 207 | 8.5 | F, A |
| Weaning ht, cm | 118 | 115 | 115 | 115 | 114 | 112 | 1.4 | F, G, S, A |

Effects: for the statistical model main effects were forage (F, f), genotype (G, g), age at weaning (A, a), sex of the calf (S, s), and month (M, m) in the case of multiple dates of collection. Uppercase letters indicate that the main effect was significant at a probability of less than 0.05; whereas, lowercase letters indicates a significance below 0.1. Interactions between main effects are indicated with an asterisk using the same uppercase and lowercase designations.

Bovine CYP3A28 gene is polymorphic, and the polymorphism is not distributed equally among Angus, Brahman, and Angus/Brahman reciprocal crosses. Milk quality and quantity were affected by the CYP3A28 polymorphism. The CYP3A28 polymorphism located at base 994 was related to breed composition, specifically, Angus versus Brahman. The presence of SNP 994 in the CYP3A28 gene in cattle did not interact with forage type to alter bovine subject reproduction or calf weaning weights while grazing endophyte-infected tall fescue. The CYP3A28 gene was related to bovine subject productivity; however, SNP 994 in CYP3A28 does not appear to be a useful tool in selecting cattle with less susceptibility to ergot alkaloid toxicity.

What is claimed is:

1. A method of determining a nucleotide in a bovine subject at a position in which a single nucleotide polymorphism is correlated with a predicted occurrence of a trait comprising: detecting a target polynucleotide in a bovine sample with at least one oligonucleotide capable of binding the target polynucleotide, wherein the target polynucleotide comprises a nucleotide at a position of the prolactin promoter corresponding to a position of SEQ ID NO:14 selected from the group consisting of position 1167 or 1286; determining the nucleotide at the single nucleotide polymorphism in the bovine subject; and correlating a guanine or adenine at a position of the target polynucleotide corresponding to position 1167 of SEQ ID NO: 14 or a cytosine or a thymine at a position of the target polynucleotide corresponding to position 1286 of SEQ ID NO: 14 to the predicted occurrence of the trait, the trait selected from the group consisting of calf height at weaning, calf weight at weaning, calving rate, breed lineage, milk protein concentration, somatic cell counts in the milk, milk butterfat concentration and calf weight at birth.

2. The method of claim 1, wherein the nucleotide at the single nucleotide polymorphism position is detected by analyzing the binding of the oligonucleotide to the target polynucleotide.

3. The method of claim 1, wherein the target polynucleotide is detected by amplification.

4. The method of claim 3 wherein the nucleotide at the SNP is determined by nucleotide sequencing or restriction fragment length polymorphism analysis.

5. A method of predicting the occurrence of a trait in a bovine subject, comprising: analyzing a sample from the bovine subject to identify a nucleotide of the bovine subject at a position of the prolactin promoter corresponding to position 1167 of SEQ ID NO:14 or position 1286 of SEQ ID NO:14; and correlating a guanine or adenine at a position corresponding to position 1167 of SEQ ID NO: 14 or a cytosine or thymine at a position corresponding to position 1286 of SEQ ID NO: 14 to predict the occurrence of the trait, the trait selected from the group consisting of calf height at weaning, calf weight at weaning, calving rate breed lineage milk protein concentration, somatic cell counts in the milk, milk butterfat concentration and calf weight at birth.

6. The method of claim 5, wherein a guanine at a position of the prolactin promoter corresponding to position 1167 of SEQ ID NO:14 correlates to the bovine subject having a trait selected from the group consisting of increased calf height at weaning, increased calf weight at weaning, and increased calvings when fed on Fescue as compared to a bovine subject having an adenine at the position.

7. The method of claim 5, wherein a guanine at a position of the prolactin promoter corresponding to position 1167 of SEQ ID NO:14 correlates to the bovine subject having a trait selected from the group consisting increased milk protein and decreased somatic cell counts in the milk as compared to a bovine subject having an adenine at the position.

8. The method of claim 5, wherein an adenine at a position of the prolactin promoter corresponding to position 1167 of SEQ ID NO:14 correlates to the bovine subject having the trait of increased calvings on Bermuda grass as compared to a bovine subject having a guanine at the position.

9. The method of claim 5, wherein a thymine at a position of the prolactin promoter corresponding to position 1286 of SEQ ID NO:14 correlates to the bovine subject having a trait selected from the group consisting of increased calf height at weaning, increased calf weight at weaning, and decreased calvings as compared to a bovine subject having a cytosine at the position.

10. The method of claim 5, wherein a cytosine at a position of the prolactin promoter corresponding to position 1286 of SEQ ID NO:14 correlates to the bovine subject having the trait of increased milk butterfat as compared to a bovine subject having a thymine at the position.

11. The method of claim 5, wherein a cytosine at a position of the prolactin promoter corresponding to position 1286 of SEQ ID NO:14 correlates to the bovine subject having the trait of increased calvings as compared to a bovine subject having a thymine at the position.

12. The method of claim 1, wherein a guanine at a position of the prolactin promoter corresponding to position 1167 of SEQ ID NO:14 correlates to the bovine subject having a trait selected from the group consisting of increased calf height at weaning, increased calf weight at weaning, and increased calvings when fed on Fescue as compared to a bovine subject having an adenine at the position.

13. The method of claim 1, wherein a guanine at a position of the prolactin promoter corresponding to position 1167 of SEQ ID NO:14 correlates to the bovine subject having a trait selected from the group consisting increased milk protein and decreased somatic cell counts in the milk as compared to a bovine subject having an adenine at the position.

14. The method of claim 1, wherein an adenine at a position of the prolactin promoter corresponding to position 1167 of SEQ ID NO:14 correlates to the bovine subject having the trait of increased calvings on Bermuda grass as compared to a bovine subject having a guanine at the position.

15. The method of claim 1, wherein a thymine at a position of the prolactin promoter corresponding to position 1286 of SEQ ID NO:14 correlates to the bovine subject having a trait selected from the group consisting of increased calf height at weaning, increased calf weight at weaning, and decreased calvings as compared to a bovine subject having a cytosine at the position.

16. The method of claim 1, wherein a cytosine at a position of the prolactin promoter corresponding to position 1286 of SEQ ID NO:14 correlates to the bovine subject having the trait of increased milk butterfat as compared to a bovine subject having a thymine at the position.

17. The method of claim 1, wherein a cytosine at a position of the prolactin promoter corresponding to position 1286 of SEQ ID NO:14 correlates to the bovine subject having the trait of increased calvings as compared to a bovine subject having a thymine at the position.

\* \* \* \* \*